United States Patent
Miyazaki et al.

(10) Patent No.: US 7,670,841 B2
(45) Date of Patent: Mar. 2, 2010

(54) METHOD OF ANALYZING C-TERMINAL AMINO ACID SEQUENCE OF PEPTIDE

(75) Inventors: Kenji Miyazaki, Minato-ku (JP); Akira Tsugita, Minato-ku (JP); Kenichi Kamijo, Minato-ku (JP); Takuji Nabetani, Chuo-ku (JP)

(73) Assignee: NEC Corporation, Tokyo (JP)

( * ) Notice: Subject to any disclaimer, the term of this patent is extended or adjusted under 35 U.S.C. 154(b) by 1013 days.

(21) Appl. No.: 10/536,824

(22) PCT Filed: Nov. 28, 2003

(86) PCT No.: PCT/JP03/15270

§ 371 (c)(1),
(2), (4) Date: May 27, 2005

(87) PCT Pub. No.: WO2004/051281

PCT Pub. Date: Jun. 17, 2004

(65) Prior Publication Data

US 2006/0030052 A1   Feb. 9, 2006

(30) Foreign Application Priority Data

Nov. 29, 2002   (JP) ............................. 2002-347777

(51) Int. Cl.
*G01N 33/00* (2006.01)
(52) U.S. Cl. ............................. 436/89; 436/86; 436/90; 435/23; 530/345
(58) Field of Classification Search ........................ None
See application file for complete search history.

(56) References Cited

U.S. PATENT DOCUMENTS 5,521,097 A * 5/1996 Uchida et al. ................. 436/86
6,046,053 A * 4/2000 Tsugita et al. ................. 436/89

FOREIGN PATENT DOCUMENTS

| JP | 05-133958 A | 5/1993 |
| JP | 6-27113 A | 2/1994 |
| JP | 10-293130 A | 11/1998 |
| JP | 2000-146983 A | 5/2000 |
| JP | 2002-189029 A | 7/2002 |
| JP | 2003-279581 A | 10/2003 |

OTHER PUBLICATIONS

Tsugita, Akira et. al., Additional possible tools for identification of proteins on one- or two-dimensional electrophoresis, 1998, Electrophoresis, vol. 19, pp. 928-938.*

(Continued)

*Primary Examiner*—Yelena G Gakh
*Assistant Examiner*—Robert Xu
(74) *Attorney, Agent, or Firm*—Sughrue Mion, PLLC

(57) ABSTRACT

The present invention provides, as a method of analyzing the C-terminal amino acid sequence of a peptide with use of reaction technique for successively releasing the C-terminal amino acids, in which undesirable side reactions, such as cleavage of a peptide bond at the middle of the peptide, can be prevented and chemical treatments therein can be carried out under widely applicable conditions in the course of successive release of the C-terminal amino acids from a peptide, such a method comprising steps of dehydrating the gel on which a target peptide that has been separated by gel electrophoresis is held in the bound state; immersing it in a mixture solution of an alkanoic acid anhydride added with a small amount of a perfluoroalkanoic acid in a dipolar aprotic solvent to re-swell the gel carrier, forming a 5-oxazolone structure, at a temperature chosen in the range of from 30° C. to 80° C., followed by the cleavage of the 5-oxazolone ring to release the C-terminal amino acids, and then specifying the C-terminal amino acid sequence of the peptide based on the measured decrease in the molecular weight of a series of reaction products resulting therefrom.

16 Claims, 4 Drawing Sheets

Truncation in Gel

Dehydration Treatment
1mL CH₃CN

Swelling Treatment
In Non-aqueous syatem
1mL 1%HFBA, 10%(CH₃CO)₂O
Solution in Formamide
50ºC, 3 hours

OTHER PUBLICATIONS

Vogt, S. et al., Effective esterification of carboxymethyl cellulose in a new non-aqueous swelling system, 1996, Polymer Bulletin, vol. 36, p. 549-555.*

A. Tsugita et al. "Reaction of Pentafluoropropionic Anhydride Vapor on Polypeptide as Revealed by Mass Spectrometry. A carboxypeptidase Mimetic Degradation", Chemistry Letters, 1992, pp. 235-238.

A. Tsugita et al. "C-terminal sequencing of protein", European J. Biochemistry, 1992. vol. 206, pp. 691-696.

K. Takamoto et al. "Carboxy-terminal degradation of peptides using perfluoroacyl anhydrides", European J. Biochemistry, 1995, vol. 228, pp. 362-372.

Miyazaki Kenji et al. "A novel C-terminal sequencing method for proteome study", Molecular and Cellular Proteomics, vol, 1, No. 9, Sep. 2002, p. 691.

Tsugita A. et al., "Additional Possible tools for identification of proteins on one- or two- dimensional electrophoresis" Electrophoresis, vol. 19, No. 6, May 1998, pp. 928-938.

Tsugita A. et al., "Reaction of Pentafluoropropionic Anhydride Vapor on Polypeptide as revealed by Mass Spectrometry. A Carboxypeptidase Mimetic Degradation" Chemistry Letters, 1992, pp. 235-238 (previously submitted with Information Disclosure Statement filed on May 27, 2005).

Miyazaki K. at al., "C-terminal sequencing method for proteins in gel by the reaction of acetic anhydride with perfluoric acid" Seikagaku—Journal of Japanese Biochemistry Society, vol. 75, No. 8, Aug. 2003, p. 924.

Kamo Masaharu et al., "A novel C-terminal stepwise sequencing method" Journal of Protein Chemistry, vol. 17, No. 6, Aug. 1998, pp. 511-512.

* cited by examiner

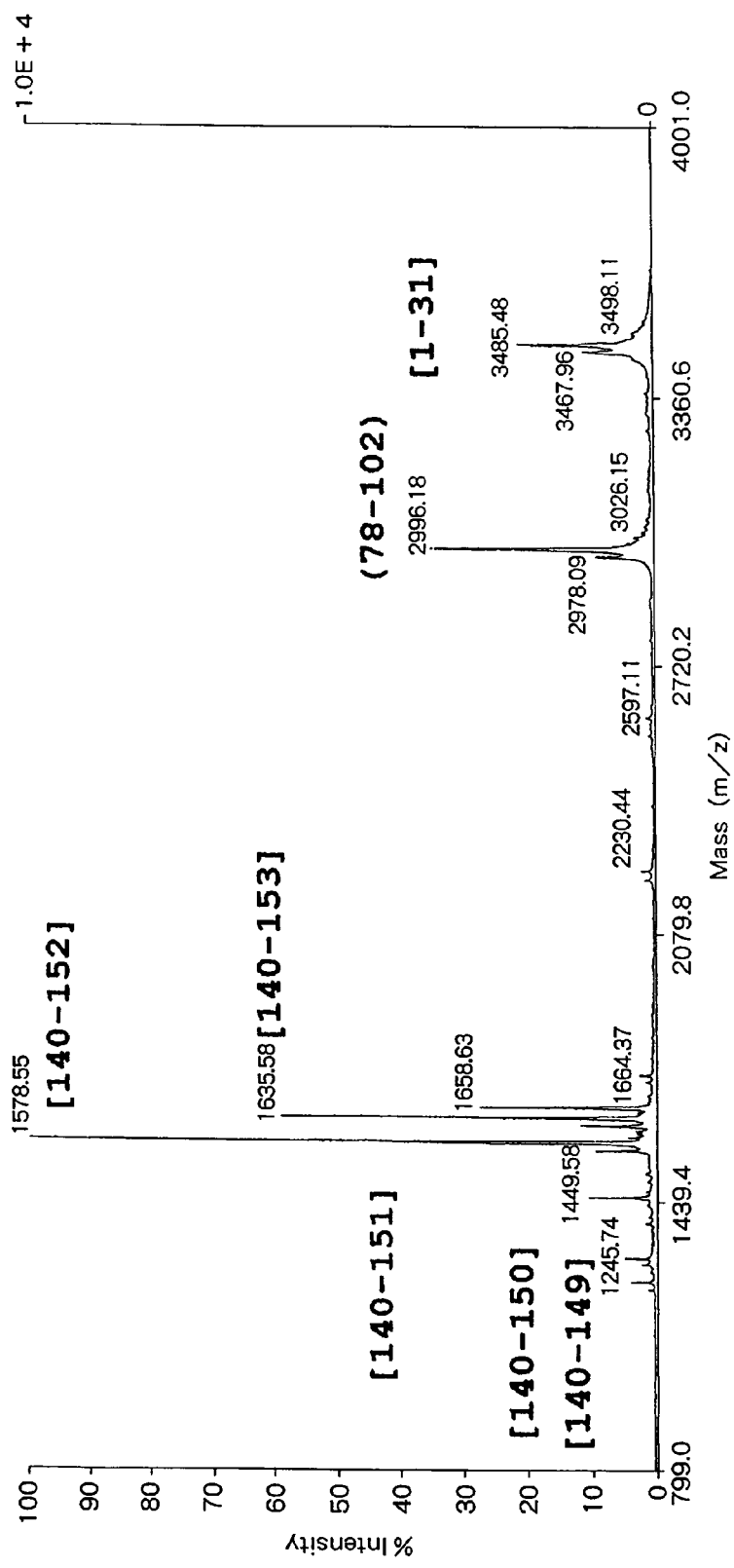

Fig. 4 myoglobin — horse

[1 – 153] mass = 17738.180
Cleavage at R

Small polar: D(7) E(13) N(3) Q(6)
Large polar: K(19) R(2) H(11)
Small non-polar: S(5) T(7) A(15) G(15)
Large non-polar: L(17) I(9) V(7) M(2) F(7) Y(2) W(2)
Special: C(0) P(4)

| | | | |
|---|---|---|---|
| K[16] + 42.04 | K[42] + 42.04 | K[45] + 42.04 | K[47] + 42.04 |
| K[50] + 42.04 | K[56] + 42.04 | K[62] + 42.04 | K[63] + 42.04 |
| K[77] + 42.04 | K[78] + 42.04 | K[79] + 42.04 | K[87] + 42.04 |
| K[96] + 42.04 | K[98] + 42.04 | K[102] + 42.04 | K[118] + 42.04 |
| K[133] + 42.04 | K[145] + 42.04 | K[147] + 42.04 | |

```
  1 G L S D G E W Q Q V L N V W G K V E A D I A G H G Q E V L I  30
 31 R I f t g h p e t l e K f d K f K h l K t e a e m K a s e d  60
 61 l K K h g t v v l t a l g g i l K K g h h e a e l K p l a    90
 91 q s h a t K h K i p i K y l e f i s d a i i h v l h s K h p 120
121 g n f g a d a q g a m t K a l e l f r N D I A A K Y K E L G 150
151 F Q G                                                      153
```

(1) [1-31] = 3444.742   (2) [32-139] = 12692.649   (3) [140-153] = 1636.809

METHOD OF ANALYZING C-TERMINAL AMINO ACID SEQUENCE OF PEPTIDE

TECHNICAL FIELD

The present invention relates to a method for analysis of C-terminal amino acid sequence of peptide, more typically to a method for identifying the C-terminal amino acid sequence, based on the decreases in molecular weight that are caused by a series of amino acids being successively eliminated, as for a peptide which can be separated by gel electrophoresis, for example, a protein composing of a peptide chain having at least 50 or more amino acids, usually 100 or more amino acids, which method comprises steps of successively releasing, by chemical technique, the C-terminal amino acids of such a peptide in a state that the peptide is still bound on a gel carrier, and determining the molecular weights of the reaction products obtained therefrom by mass spectrometry.

BACKGROUND ART

With respect to peptides and proteins collected from nature, the identification of their amino acid sequences are essential information to make a study of the biological properties and functions of the peptides and proteins in question. Currently, the full-length amino acid sequences for peptides and proteins are determined as deduced amino acid sequences, based on corresponding gene information thereof, for instance, nucleotide sequences of the genomic genes or c-DNAs produced from m-RNAs which encode their peptides. However, in identifying the genomic genes or the c-DNAs produced from m-RNAs which encode these peptides, the knowledge of partial amino acid sequences of the peptides is still required.

It is generally considered that, as the knowledge of the partial amino acid sequences of peptide, the N-terminal amino acid sequence and C-terminal amino acid sequence of peptide are particularly useful. Specifically, for example, in selecting a c-DNA which encodes an aimed peptide from a c-DNA library prepared from a large number of m-RNAs, if the N-terminal amino acid sequence and C-terminal amino acid sequence thereof are known, the aimed c-DNA can be selected by using nucleic acid probes that are produced based on said amino acid sequences of the two termini. Alternatively, the aimed c-DNA can be amplified selectively by applying PCR with use of oligonucleotide primers that are produced based on the amino acid sequences of the two termini.

As the method for analyzing the N-terminal amino acid sequence of a peptide, there has been conventionally used a method of subjecting a pure peptide sample obtained by isolation and purification to Edman degradation to successively degrade the N-terminal amino acids therefrom and identify the resulting amino acid derivatives. Meanwhile, as the method for analyzing the C-terminal amino acid sequence of a peptide, there has been proposed a method comprising steps of releasing the C-terminal amino acids successively from such a pure peptide sample by means of chemical technique and identifying the C-terminal amino acids released thereby, based on the molecular weight differences between the original peptide and truncated peptides that are obtained as reaction products therefrom. As the process for releasing the C-terminal amino acids successively by means of chemical technique, there is proposed, for example, a process comprising steps of allowing a vapor generated from a high concentration aqueous solution of pentafluoropropanoic acid ($CF_3CF_2COOH$) or a high concentration aqueous solution of heptafluorobutanoic acid ($CF_3CF_2CF_2COOH$), to act on a dried pure peptide sample under heating up condition of at 90° C., and thereby carrying out selective hydrolysis of the C-terminal amino acids, which is enhanced by said perfluoroalkanoic acid [Tsugita, A. et al., Eur. J. Biochem. 206, 691-696 (1992)]. In addition, there is also proposed a process using, in place of said high concentration aqueous solution of a perfluoroalkanoic acid, a solution of pentafluoropropanoic acid anhydride [$(CF_3CF_2CO)_2O$] in acetonitrile or a solution of heptafluorobutanoic acid anhydride [$(CF_3CF_2CF_2CO)_2O$] in acetonitrile, which process comprises steps of allowing a vapor generated from the solution, to act on a dried peptide under cooling down condition, for example, at −18° C., and thereby conducting selective release of the C-terminal amino acids, which is forced by said perfluoroalkanoic acid anhydride [Tsugita, A. et al., Chem. Lett. 1992, 235-238; Takamoto, K. et al., Eur. J. Biochem. 228, 362-372 (1995)].

In said method for selectively releasing the C-terminal amino acids by allowing a perfluoroalkanoic acid or a perfluoroalkanoic acid anhydride, which are supplied in vapor phase as a vapor thereof, to act on a dried pure peptide sample, it has been reported that an oxazolone ring structure is once formed from the C-terminal amino acids, as a reaction intermediate, through a dehydration reaction shown by the following reaction scheme (I):

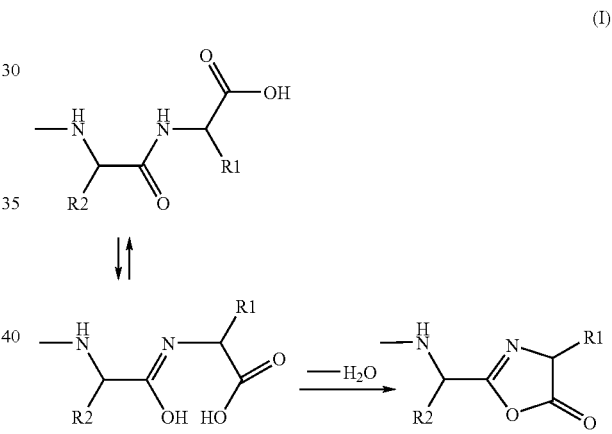

and then, the perfluoroalkanoic acid acts on the oxazolone ring to give rise to a reaction shown by the following reaction scheme (II):

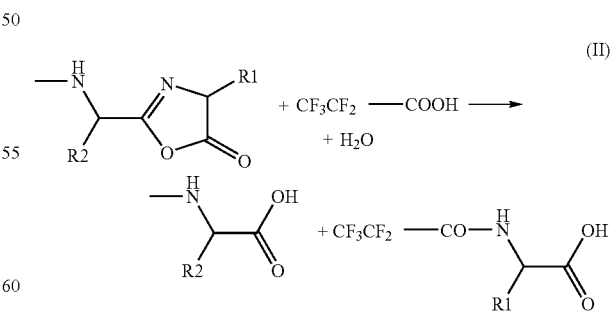

as a result, reaction of selectively releasing the C-terminal amino acids therefrom is achieved.

As the above reaction of selectively releasing the C-terminal amino acid proceeds successively, there is obtained, at a timing when a given treatment time has passed, a mixture comprising a series of reaction products in which one to ten odd amino acid residues have been removed from the C-terminus of the original peptide, respectively. This mixture comprising a series of reaction products is subjected to mass spectrometry to measure the masses of the ion species derived from the reaction products, whereby can be obtained a series of peaks exhibiting the mass differences, which reflect the C-terminal amino acid sequence. Specifically explaining, the individual reaction products are formed in reaction of successively releasing the C-terminal amino acids from the original peptide; hence, for example, a set of reaction products including several members in series, where up to several amino acid residues have been removed from the original peptide, are subjected to mass spectrometry and, thereby, the masses of corresponding ion species thereto can be analyzed collectively, which enables determination of C-terminal amino acid sequence of such several amino acid residues at one time.

Incidentally, for example, the information of C-terminal amino acid sequence used in production of nucleic acid probe or primer may originally be, in terms of the nucleotide sequence which codes such amino acid sequence, about 18 to 24 bases and accordingly about 6 to 8 amino acids. The identification of C-terminal amino acid sequence of up to ten odd amino acid residues is required only in very rare cases. Therefore, the above methods for preparation of treated sample comprising a series of reaction products, in which all the removals extending up to 10 amino acid resides are included, by the reaction of releasing the C-terminal amino acids from the dried peptide, where a vapor of a perfluoroalkanoic acid or a perfluoroalkanoic acid anhydride are supplied in vapor phase and allowed to act thereon, are suitable for the above-mentioned purposes.

DISCLOSURE OF THE INVENTION

The above-mentioned methods in which the vapor of a perfluoroalkanoic acid or a perfluoroalkanoic acid anhydride is supplied in vapor phase to act on a dried peptide is a useful method for clarifying the C-terminal amino acid sequence of the peptide; however, since the reaction uses a reaction reagent being supplied in vapor phase, the peptide sample to be analyzed is in advance subjected to isolation and purification and further to treatment for drying up, and then a pure peptide sample prepared thereby is applied to said method for analysis. Therefore, the availability of such a pure peptide sample that is dried up, post to in advance isolation and purification, has been a prerequisite enabling the analysis using a vapor-phase reaction reagent.

Meanwhile, with respect to the method for confirming whether or not a known peptide or protein whose amino acid sequence has been identified is present in a particular cell tissue, when a mixed sample containing a large number of peptides and proteins collected from a particular cell tissue is separated by gel electrophoresis by, for example, there is being widely used a technique of separation by means of gel electrophoresis, for instance, a SDS-PAGE method, which is method for confirming the presence of the individual peptides and proteins exhibiting respective spots corresponding to their molecular weights on a polyacrylamide gel carrier. Further, there is being widely used a method for separating the individual peptides and proteins as respective spots based on their isoelectric points by means of isoelectric focussing technique. Furthermore, in two-dimensional electrophoresis, two types of electrophoresis are combined and, consequently, peptides and proteins are isolated as spots being two-dimensionally divided in accordance with difference in their molecular weights and isoelectric points. In such a case, it is necessary to verify whether or not a particular peptide that gives rise to the spot detected on a gel carrier is indeed an intended peptide.

In verifying that it is an intended peptide, there is being used, in some cases, for example, a method of reacting it with an antibody showing reactivity specific to the intended peptide to detect such an antigen-antibody reaction. This verification method, however, is usable only when the antibody showing specific reactivity is available.

Therefore, it is desired to provide a method which need not use an antibody showing specific reactivity and which can verify that a particular peptide appearing as a spot on a gel carrier is truly an intended peptide.

Since the proteins to which the verification method using an antibody-antigen reaction is applicable are limited, there is also being used other verification method which uses a technique called a peptide mass fingerprint (PMF) method. In this PMF method, in such a case that when an intended peptide being subjected to enzymatic cleavage using a protease having cleavage site specificity, for example, such as trypsin, the molecular weights of the individual peptide fragments formed thereby have been known beforehand, an isolated peptide is fragmentized by the same enzymatic cleavage; the molecular weights of the individual peptide fragments therefrom are measured by mass spectrometry and compared with the molecular weights of peptide fragments recorded in the data base as for the intended peptide; whereby, the identify thereof is established.

Further, when, in analysis of peptide by mass spectrometry, there is used a MS/MS method, such as a TOF-SIMS method, in which as for ion species being separated by MALDI-TOF type mass spectrometry, secondary ion species therefrom, which are generated by an electron beam irradiation, are further subjected to mass spectrometry, whereby the information regarding the partial composition of each peptide fragment can be available. By using the MS/MS method, for example, the N-terminal and C-terminal sequences of peptide can be identified in certain case.

When the above-mentioned PMF method in combination with MS/MS method is used, as compared with the case that the antigen-antibody reaction is used, the range of peptides to which the PMF method is applicable is remarkably extended; however, the range is limited to those proteins or peptides whose amino acid sequences are known and for which the data bases concerning with identification of the ion species derived from each of their peptide fragments are fully equipped. Therefore, it is desired to provide a technique which is be more commonly applicable to verify whether or not a peptide that gives rise to a spot detected on a gel carrier is just a target peptide of which the amino acid sequence has been known.

Regarding a known peptide or protein whose amino acid sequence has been known, when separation by means of gel electrophoresis is conducted under the same conditions, it gives a spot on a peculiar position at a considerable reproducibility. Therefore, the present inventors have gotten such a conception that, as the above-mentioned verification technique, such a method in which the partial amino acid sequence of a peptide giving a spot on the corresponding position is analyzed to verifying its identity with the corresponding partial sequence included in the known amino acid sequence may be usable as for a technique that will meet the aforementioned requirement. More particularly, the present inventors has conceived that in the case where SDS-PAGE method or two-dimensional electrophoresis is employed, when the approximate molecular weight of a peptide giving a band or a spot on a gel carrier is quickly identified and the C-terminal amino acid sequence thereof is determined, it may be easy to verify whether or not the peptide giving such a spot is indeed an intended peptide by checking whether they are identical with the molecular weight and C-terminal amino acid sequence of the known peptide of which amino acid sequence has been known.

In reducing the concept to practice, it is possible in principle to choose such a process comprising steps of cutting off the piece for a peptide giving the spot detected on the gel carrier, dissolving the gel to extract the peptide therefrom, conducting the treatment for isolating and recovering again the peptide from the resulting liquid phase, and then applying a conventional technique for analysis of the C-terminal amino acid sequence to the peptide. However, in such treatment for isolating and recovering again the peptide from liquid phase, the actual recovery efficiency is not always high; as for peptides having a large number of amino acid residues, the recovery efficiency is extremely low in many cases; therefore, the present inventors has found that, in order to reduce the above-mentioned conception to practice as for wider spectrum of targets to be examined, it is necessary to analyze the C-terminal amino acid sequence of the target peptide in a state that it is bound on a gel carrier.

The present invention is intended to solve the above-mentioned problems and the aim of the present invention is to provide a reaction technique for successive release of C-terminal amino acids of peptide, in which, when a target peptide separated by gel electrophoresis, in particular, such a peptide chain having many amino acid residues as proteins, is subjected, in a state that said peptide is bound on a gel carrier, to successive release of C-terminal amino acids according to a reaction mechanism via the formation of an oxazolone ring structure, undesirable side reactions such as cleavage of peptide bond in the middle of peptide chain can be suppressed and the successive release per se can be carried out under widely applicable conditions. More particularly, the aim of the present invention is to provide a method for analysis of C-terminal amino acid sequence of peptide using a novel reaction technique for successive release of C-terminal amino acids of peptide, in which, when water is removed from the gel substance to dry up the peptide in a state that it is bound on the gel carrier, and then the C-terminal amino acids thereof are successively released, reaction reagents initiating said chemical treatment can be uniformly supplied to the peptide that is staying in the porous framework formed within the gel, and the treatment can be carried out under mild conditions near room temperature.

The present inventors made an energetic study and investigation repeatedly in order to solve the above-mentioned problems. As a result, the present inventors confirmed the followings. A gel substance used in gel electrophoresis has a fine-porous framework through which a peptide can migrate, and holds water therein; when a reaction of oxazolone ring formation is conducted, the water contained in the gel substance need be removed; meanwhile, when the water is removed from the gel substance to dry up, the water filled in the fine-porous framework is taken away, which results in a decrease in the bulk size of the whole gel and makes it difficult to uniformly feed a reaction reagent in vapor form into the fine-porous framework deflated.

Further, the present inventors made an investigation on how to feed a reaction reagent. As a result, the present inventors found the following. When the gel having the fine-porous framework inside, which is deflated owing to the treatment for dehydration, is reswollen by using an organic solvent that contains no water and can dissolve reaction reagents such as perfluoroalkanoic acid and acid anhydride, and thereby the pore of the fine-porous framework therein is inflated, a reaction reagent dissolved in said organic solvent can be uniformly fed into the gel inside via the pore thereof. More particularly, the present inventors found the following. By using a mixed solution of an alkanoic acid anhydride added with a small amount of a perfluoroalkanoic acid in relative ratio thereto dissolved in a dipolar aprotic solvent that is capable of infiltrating into the gel substance dehydrated and keeping it in a swollen state, the gel carrier is immersed in the mixed solution to allow the alkanoic acid anhydride and the perfluoroalkanoic acid to act on the target peptide sample that is kept in the bound state, whereby a series of reactions can be carried out which include formation of oxazolone ring structure at the C terminus, subsequent dissociation of the C-terminal amino acid residue, and further formation of oxazolone ring structure. In addition to these findings, the present inventors confirmed that the truncated peptides, which are reaction products resulting from said reactions, as well as the original peptide can not diffuse or be extracted away from the gel swollen by the dipolar aprotic solvent, and thus they can be held in a state that they are bound on the gel carrier, which both can be analyzed simultaneously by mass spectrometry. The present invention has been completed therewith.

Thus, according to the present invention, there is provided a method for analyzing the C-terminal amino acid sequence of a peptide to be examined, which method comprises steps of:

preparing a mixture containing a series of reaction products obtained by process for releasing the C-terminal amino acids successively from the target peptide to be examined by chemical procedure, analyzing the difference of molecular weight between said series of reaction products and the original peptide by means of mass spectrometry to measure the decreases in molecular weight associated with the successive release of the C-terminal amino acid, and identifying a series of the amino acids removed successively, based on a series of the measured decreases in molecular weight and arranging those in sequence from the C-terminus to obtain the information of the C-terminal amino acid sequence, wherein in the step of releasing the C-terminal amino acids successively, the treatment for the sample of the target peptide that has been subjected to separation by gel electrophoresis and is maintained in a state that it is bound on a gel carrier is made through the following process that is conducted in a state that the sample of the target peptide is kept on the gel carrier, which process comprises steps of:

removing the water solvent impregnated into the gel carrier by dilution with use of a polar aprotic solvent having no solvency for the gel substance and having affinity for water, to conduct a dehydration treatment for the gel carrier, immersing, at a temperature selected in a range of 30° C. to 80° C., the gel carrier on which the target peptide sample is still bound after said dehydration treatment in a mixed solution of an alkanoic acid anhydride added with a small amount of a perfluoroalkanoic acid in relative ratio thereto dissolved in a dipolar aprotic solvent that is capable of infiltrating into the gel substance and keeping it in a swollen state, to allow the alkanoic acid anhydride and the perfluoroalkanoic acid to act on the target peptide sample being kept in the bound state; thereby, successive release of the C-terminal amino acids results from the reaction process with use of the mixed solution in which formed is a 5-oxazolone-ring structure represented by the following general formula (III):

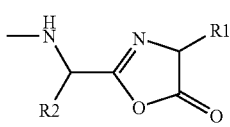

wherein R1 is a side chain of the C-terminal amino acid of the peptide and R2 is a side chain of the amino acid residue positioned just before the C-terminal amino acid, followed by the cleavage of the 5-oxazolone-ring, and removing the mixed solution used in the reaction for successive release of C-terminal amino acids, by dilution with use of a polar aprotic solvent having no solvency for the gel substance and having affinity for the perfluoroalkanoic acid and the alkanoic acid anhydride as well as the dipolar aprotic solvent, to conduct termination of the releasing reaction and removal of the reaction reagents therefor; and wherein the mixture containing the original peptide and a series of reaction products, which is obtained by conducting said process for successive release of C-terminal amino acids in a state that the sample is bound on a gel carrier, is subjected to the above-mentioned mass spectrometry step.

In that case, it is preferred that a symmetric anhydride of an alkanoic acid having 2 to 4 carbon atoms is used as the alkanoic acid anhydride contained in said mixed solution where a small amount of a perfluoroalkanoic acid in relative ratio to the alkanoic acid anhydride is dissolved. Further, it is desired that a symmetric anhydride of a linear-chain alkanoic acid having 2 to 4 carbon atoms is used as said symmetric anhydride of an alkanoic acid having 2 to 4 carbon atoms. It is more preferred that acetic anhydride, for example, is used as the alkanoic acid anhydride contained in said mixed solution where a small amount of a perfluoroalkanoic acid in relative ratio to the alkanoic acid anhydride is dissolved.

Meanwhile, it is preferred that a perfluoroalkanoic acid of which a pKa is in the range of 0.3 to 2.5 is used as the perfluoroalkanoic acid contained in the mixed solution where a small amount of the perfluoroalkanoic acid in relative ratio to the alkanoic acid anhydride is dissolved. For example, a perfluoroalkanoic acid having 2 to 4 carbon atoms may be used as the perfluoroalkanoic acid contained in said mixed solution where a small amount of the perfluoroalkanoic acid in relative ratio to the alkanoic acid anhydride is dissolved. Further, it is more desired that a linear-chain perfluoroalkanoic acid having 2 to 4 carbon atoms is used as said perfluoroalkanoic acid having 2 to 4 carbon atoms. Incidentally, it is more desired that in the mixed solution where a small amount of the perfluoroalkanoic acid in relative ratio to the alkanoic acid anhydride is dissolved, the content ratio of the alkanoic acid anhydride and the perfluoroalkanoic acid is selected in the range of 1 to 20 volumes of the perfluoroalkanoic acid per 100 volumes of the alkanoic acid anhydride.

In addition, it is further desired that in said reaction treatment in the mixed solution using a dipolar aprotic solvent, said reaction system therefor is kept in a dry atmosphere wherein not only water but also oxygen have been eliminated Furthermore, in the method for analyzing the C-terminal amino acid sequence of a peptide according to the present invention, it is preferred that, in said process of successive release of C-terminal amino acids, after the step of removing the mixed solution by dilution with use of the polar aprotic solvent to conduct termination of the release reaction and removal of the reaction reagents therefor, there is provided additional step for hydrolysis treatment and then redehydration treatment, in which step the hydrolysis treatment for said mixture comprising a series of reaction products obtained by the reaction for successive release of C-terminal amino acids is conducted by immersing the gel carrier in an aqueous solution dissolving a basic nitrogen-containing aromatic compound or a tertiary amine compound therein to allow a water molecule to act, in the presence of said basic nitrogen-containing organic compound, on said peptides of the reaction products being still bound on the gel carrier; and then, the redehydration treatment for the gel carrier is performed by removing said aqueous solution infiltrated into the gel carrier by dilution with use of a polar aprotic solvent having no solvency for the gel substance and having affinity for water.

Alternatively, said additional step for hydrolysis treatment and then redehydration treatment may be performed in such a way that, after the temperature is cooled down to stop the degrading reaction, in place of the step of removing the mixed solution by dilution with use of the polar aprotic solvent to conduct termination of the release reaction and removal of the reaction reagents therefor, the hydrolysis treatment for said mixture comprising a series of reaction products obtained by the reaction for successive release of C-terminal amino acids is conducted by immersing the gel carrier in an aqueous solution dissolving a basic nitrogen-containing aromatic compound or a tertiary amine compound therein to allow a water molecule to act, in the presence of said basic nitrogen-containing organic compound, on said peptides of the reaction products being still bound on the gel carrier;

simultaneously, said reaction reagents comprising the alkanoic acid anhydride in combination with the perfluoroalkanoic acid is inactivated and is eluted out; and then the redehydration treatment for the gel carrier is carried out by removing said aqueous solution infiltrated into the gel carrier by dilution with use of a polar aprotic solvent having no solvency for the gel substance and having affinity for water.

Furthermore, it is more preferred that, in said process of successive release of C-terminal amino acids, prior to said reaction treatment in the mixed solution using the dipolar aprotic solvent, there is provided a further step of pretreatment for the target peptide sample that is still bound on the gel carrier after carrying out said step for dehydration treatment, in which step applying N-acylation protection by the acyl group derived from the alkanoic acid constituting said alkanoic acid anhydride, to the N-terminal amino group of the target peptide with use of a solution of an alkanoic acid anhydride dissolved in a dipolar aprotic solvent that is capable of infiltrating into the gel substance and keeping it in a swollen state is conducted by immersing, at a temperature selected in a range of 30° C. to 80° C., the gel carrier in the solution of the alkanoic acid anhydride to allow the alkanoic acid anhydride to act on the target peptide sample that is kept in the bound state; and then removal of said solution is carried out by dilution with use of a polar aprotic solvent having no solvency for the gel substance and having affinity for the alkanoic acid anhydride as well as the dipolar aprotic solvent, to conduct termination of the N-acylation reaction and removal of the reaction reagent therefor. In this case, it is further preferred that the same alkanoic acid anhydride is employed for the alkanoic acid anhydride used for applying N-acylation protection to the N-terminal of peptide in the pretreatment step, as well as for the alkanoic acid anhydride used in the subsequent step of successive release of C-terminal amino acids.

Alternatively, said pretreatment step of performing N-acylation may be conducted in such a way that, prior to said reaction treatment in the mixed solution using the dipolar aprotic solvent, applying N-acylation protection by the acyl group derived from the alkanoic acid constituting said alkanoic acid anhydride, to the N-terminal amino group of the target peptide with use of a solution of an alkanoic acid anhydride dissolved in a dipolar aprotic solvent that is capable of infiltrating into the gel substance and keeping it in a swollen state is conducted by immersing, at a temperature selected in a range of 30° C. to 80° C., the gel carrier in the solution of the alkanoic acid anhydride to allow the alkanoic acid anhydride to act on the target peptide sample that is kept in the bound state;

after that, the temperature is cooled down to stop the acylation reaction, and water is added thereto to perform said inactivation treatment of the alkanoic acid anhydride and elute it out from the gel; and then the redehydration treatment for the gel carrier is carried out by removing the water therefrom by dilution with use of a polar aprotic solvent having no solvency for the gel substance and having affinity for water and said alkanoic acid anhydride as well as the alkanoic acid corresponding thereto.

On the other hand, it is generally desired that preparation of the target peptide sample that has been subjected to separation by gel electrophoresis and is maintained in a state that it is bound on a gel carrier is carried out by means of electrophoresis using a polyacrylamide gel as the gel carrier. Meanwhile, it is further preferred that in said step of analyzing the series of reaction products and the original peptide by mass spectrometry, a MALDI-TOF type mass spectrometry is selected as the mass spectrometry.

BRIEF DESCRIPTION OF THE DRAWINGS

FIG. 3 is a chart showing an example of the mass spectrometry spectrum of a mixture of reaction products that are obtained by successive release of C-terminal amino acids from a globin peptide chain of horse myoglobin by means of the treatment technique for successively releasing the C-terminal amino acids from an isolated and dried peptide, as described in Reference Example.

FIG. 4 is a drawing showing the lysine residues to undergo N-acylation, contained in the globin peptide chain of horse myoglobin, and partial amino acid sequences of 1-31 and 140-153 fragments that will be generated by cleaving the peptide bond at the C-terminal side of each alginine residue due to digestion by trypsin.

BEST MODE FOR CARRYING OUT THE INVENTION

Figure 1:
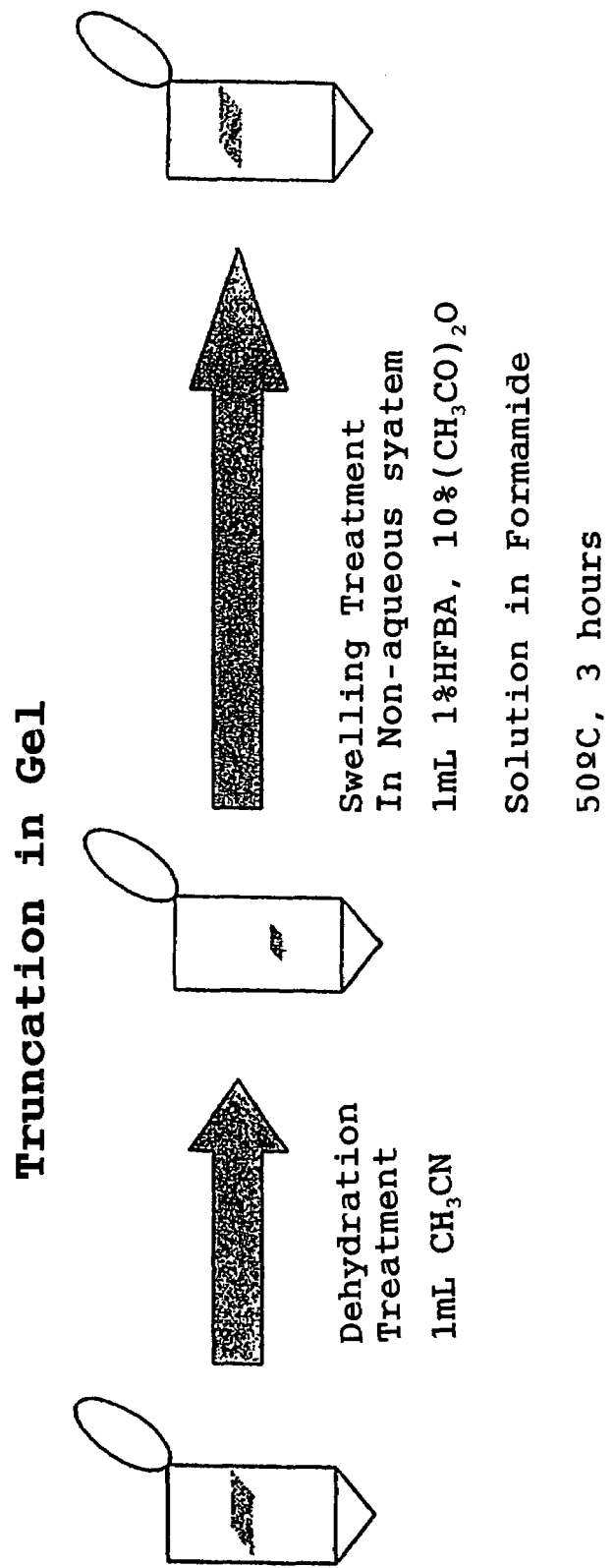
FIG. 1 is a drawing showing a process flow illustrating the characteristic features of the procedures for operation, which are employed in the treatment for successively releasing the C-terminal amino acids from a peptide according to the present invention.

The present invention is explained in more detail below.

The method for analysis of C-terminal amino acid sequence of peptide according to the present invention basically utilizes a technique which comprises steps of releasing, from a peptide to be examined, its C-terminal amino acids successively to prepare a series of reaction products each having a sequential truncation in peptide chain, and identifying the released amino acids based on the differences between the molecular weights of the series of reaction products and the molecular weight of the original peptide. More particularly, mass spectrometry is used as the means for measuring the molecular weights of the series of reaction products and the molecular weight of the original peptide. It is preferred to use a mass spectrometry apparatus which is more suitable for measurement under such conditions as to give rise to, in the ionization step thereof, no partial removal of atomic group from amino acid residues composing the peptide, for example, such as a MALDI-TOF-MS (Matrix Assisted Laser Desorption Ionization Time-of-Flight Mass Spectrometry) apparatus.

Meanwhile, the greatest feature of the analysis method according to the present invention is as follows. That is, in the step of successive release of C-terminal amino acids, a target peptide is beforehand separated by gel electrophoresis and, in a state bound on the gel carrier used in the electrophoresis, is subjected to a series of reactions; a series of reaction products obtained finally and the original peptide are isolated from the gel carrier right before they are measured for molecular weights by mass spectrometry; thereby, a measurement of high reproducibility is made possible even when the amount of the peptide sample used is small. In this case, by using a mass spectrometry apparatus, for example, a MALDI-TOF-MS apparatus, it is made possible to measure only the target peptide giving a single spot on the gel carrier, at a high molecular weight resolution and accuracy. In other words, as for a plurality of kinds of peptide samples beforehand separated by gel electrophoresis to compose respective spots (or bands), after simultaneous operation of successive release of C-terminal amino acids therefrom is carried out, the gel pieces corresponding to each of spots (or bands) is cut apart, and subjected to mass spectrometry; thereby it is possible to accomplish analysis of the C-terminal amino acid sequence for a plurality of kinds of peptide samples included in the original sample, at high efficiency and uniformity.

Incidentally, with respect to the gel substance used at the step of beforehand separation by means of gel electrophoresis, there are appropriately adjusted the conditions under which a plurality of different peptides ranking within a particular molecular weight range can give respective spots (or bands) well separated from each other, specifically, the sizes of the pores included in the fine-porous structure that is formed inside the gel, by selecting the content ratio of a polyacrylamide composing the gel. As a result, there are localized, on the spots (or bands) separated from each other, peptides different in electrophoresis speed owing to the differences in molecular weight of peptide chain thereof and amount of surface electric charge thereon, in, for example, two-dimensional electrophoresis or SDS-PAGE method.

Such peptides is held inside the fine-porous structure formed in the gel; when removing the water included in the gel substance, the method using a polar aprotic solvent which does not dissolve the gel substance but has affinity for water is employed for eluting out only the water solvent thereof by diluting into the polar aprotic solvent, whereby the aimed peptides can be held in a state that they are bound on the gel carrier positioning at the spots (or bands) separated from each other, even after completion of such operations for dehydration treatment. The polar aprotic solvent used in such dehydration treatment is generally inferior to water in the affinity for the gel substance such as polyacrylamide constructing the gel; therefore, the bulk volume of the gel decreases with the removal of the water solvent that has had solvation with the pore surfaces, which has supported the sizes of the pores of the fine-porous structure in the gel substance. As preferable polar aprotic solvents used in the dehydration treatment, there can be mentioned, for example, nitriles having 4 or less carbon atoms such as acetonitrile ($CH_3CN$) and ketones having 4 or less carbon atoms such as acetone and the like, which are superior in the affinity for water, when there is used a polyacrylamide gel.

Thus, when said polar aprotic solvent used in the dehydration is vaporized for dryness, the gel carrier decreases in bulk volume and shrinks; as a result, it becomes impossible to uniformly feed, inside the gel carrier via the narrowed pores of the fine-porous structure of gel carrier, a vapor of a reaction reagent, namely a perfluoroalkanoic acid or its anhydride, such as pentafluoropropanoic acid $CF_3CF_2COOH$, to allow the reaction reagent to act on the C-terminal amino acids of peptide.

In the method of the present invention, the gel carrier whose bulk volume has decreased and shrunken owing to the dehydration treatment mentioned above, is reswollen using a dipolar aprotic solvent infiltratable into the gel substance and capable of keeping it in a swollen state, whereby the pores in the fine-porous structure are widened. In this case, by using a mixed solution of an alkanoic acid anhydride with a small amount of a perfluoroalkanoic acid in relative ratio thereto dissolved in the dipolar aprotic solvent used for swelling of gel, the alkanoic acid anhydride and the perfluoroalkanoic acid are fed uniformly to the peptide bound in the fine-porous structure of gel carrier and allowed to act thereon.

The alkanoic acid anhydride and the perfluoroalkanoic acid first give rise to formation, at the C-terminus of the peptide, of a 5-oxazolone structure represented by the following general formula (III):

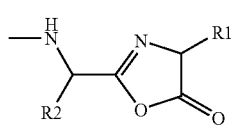

(III)

wherein R1 is a side chain of the C-terminal amino acid of the peptide and R2 is a side chain of the amino acid residue positioned just before the C-terminal amino acid, for example, through the reaction mechanism described below.

The reaction for formation of 5-oxazolone ring is expressed on the whole by the following reaction schem (I):

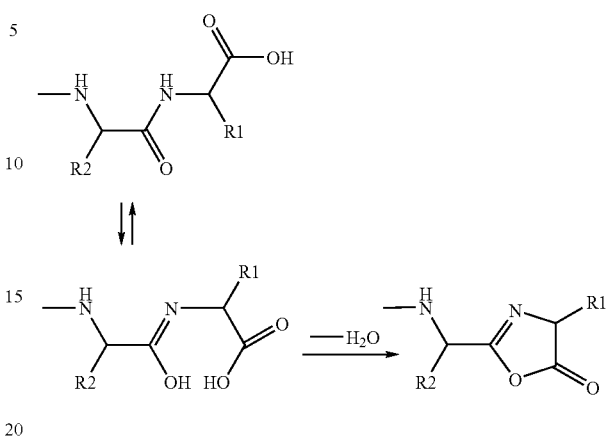

(I)

In such process for successive release of C-terminal amino acids of peptide according to the present invention, first, the perfluoroalkanoic acid is allowed to act as a proton donor on the dried peptide at the stage of keto-enol tautomerism represented by the following reaction scheme (Ia):

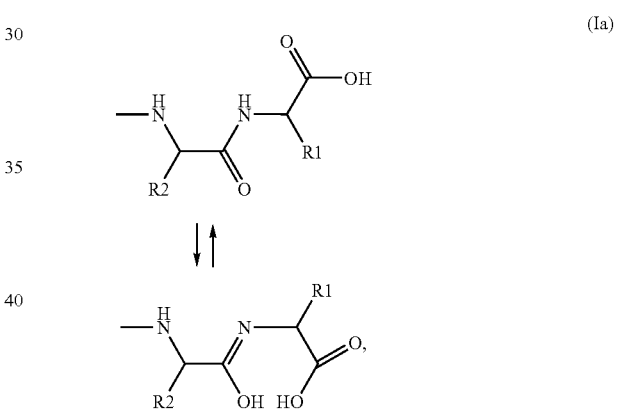

(Ia)

and thereby the ratio of enol form is heightened.

Then, an intramolecular ester bond is formed between the hydroxy group exposed in the enol type and the C-terminal carboxy group to complete the 5-oxazolone ring-formation. In this case, in the process for successive release of C-terminal amino acids according to the present invention, there is used an alkanoic acid anhydride as a reagent for activation of C-terminal carboxy group, and the enol form is converted into, for example, an asymmetric acid anhydride such as shown in the following reaction scheme (Ib):

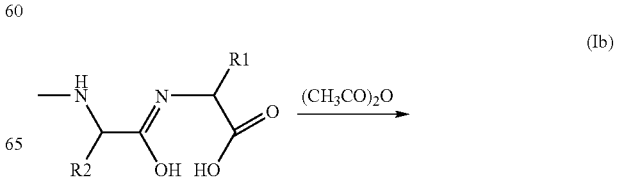

(Ib)

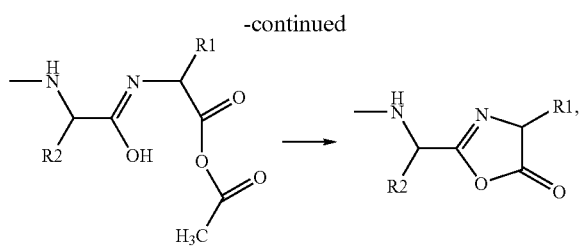

and thus the activated C-terminal carboxy group is involved in the reaction. The alkanoic acid anhydride, as compared with the perfluoroalkanoic acid, is contained in a higher concentration; thereby, the above reaction can proceed under a mild temperature condition, and typically the reaction temperature can be selected in a range of 30° C. to 80° C.

Meanwhile, in the process for selective release of C-terminal amino acids according to the present invention, as for the perfluoroalkanoic acid used therein, its proton donatability is utilized, and thus there is preferably used a perfluoroalkanoic acid of which pKa is within a range of 0.3 to 2.5. Further, more suitable is a perfluoroalkanoic acid having 2 to 4 carbon atoms, which is dissolvable uniformly in the dipolar aprotic solvent used therefor, at said reaction temperature; and much more suitable is a linear-chain perfluoroalkanoic acid having 2 to 4 carbon atoms; and in particular, it is further more desirable to utilize trifluoroacetic acid ($CF_3COOH$), pentafluoropropanoic acid ($CF_3CF_2COOH$) or heptafluorobutanoic acid ($CF_3CF_2CF_2COOH$).

As for the alkanoic acid anhydride used therewith, there is preferred one giving rise to an appropriate reactivity when heated up to the reaction temperature. Therefore, it is preferred to use a symmetric anhydride of an alkanoic acid having 2 to 4 carbon atoms. Among those, a symmetric anhydride of a linear-chain alkanoic acid having 2 to 4 carbon atoms is more preferably used as said symmetric anhydride and, in particular, a symmetric anhydride of a linear-chain alkanoic acid having 2 carbon atoms, i.e. acetic anhydride is used suitably therefor. As the alkanoic acid anhydride is employed to activate the C-terminal carboxy group, it is preferred to use those that hardly induce steric hindrance, and, in this respect as well, the acetic anhydride or the like as exemplified above is more suitable.

Further, the alkanoic acid anhydride used as a reagent for the afore-mentioned activating is consumed with the progress of reaction; therefore, it is desired to dissolve the anhydride beforehand in the dipolar aprotic solvent used for swelling of gel, in a large excess relative to the amount to be consumed in the reaction with peptide, in order to suppress the reduction in its concentration. Specifically, as for the ratio of alkanoic acid anhydride and perfluoroalkanoic acid in the mixed solution used for swelling of gel, it is desirable to select in a range of 1 to 20 volumes of perfluoroalkanoic acid per 100 volumes of alkanoic acid anhydride, and in that case, it is more desirable to choose the concentration of alkanoic acid anhydride in dipolar aprotic solvent in a range of 10 to 30% by volume. The reaction time is desired to be appropriately selected dependently upon the reaction temperature and the contents of alkanoic acid anhydride and perfluoroalkanoic acid in dipolar aprotic solvent and also in view of the time required for swelling of the gel carrier that is shrunk in association with the dehydration treatment using a polar aprotic solvent. For example, the time for a polyacrylamide gel (12.5% by mass) that is required to achieve the reswelling of the gel carrier by immersing it in a dipolar aprotic solvent such as formamide, after the afore-mentioned dehydration treatment using acetonitrile has been carried out, is about 3 hours, for instance, at 40° C.; therefore, the overall reaction time is selected so as to be summed up with a time required to achieve selective release of C-terminal amino acids up to intended amino acid residues, after the finish of reswelling step for said gel carrier.

Meanwhile, as for the dipolar aprotic solvent used for reswelling of gel, there is preferred an organic solvent that has a relatively small molecular size and excellent affinity for the gel substance, which can infiltrate into the gel substance and maintain it in a swollen state. It is further preferred that the solvent shows such a high bipolarity as, at the stage of keto-enol tautomerism represented by the above-mentioned scheme (Ia), the ratio of enol form can be maintained and that the solvent has high solvency toward the alkanoic acid anhydride and perfluoroalkanoic acid, both of which are solute molecules, as well as the alkanoic acid, which is a by-product formed therefrom. In addition, a dipolar aprotic solvent that is low in volatility at the above-mentioned reaction temperature is more preferred. For instance, examples that meet all the requirements mentioned above sufficiently may include formamide ($HCONH_2$), when a polyacrylamide gel is used.

The afore-mentioned dipolar aprotic solvent having high solvency toward the alkanoic acid anhydride and perfluoroalkanoic acid as well as the alkanoic acid, which is a by-product formed in the reaction, can dissolve even water molecules easily. Therefore, in said treatment for reaction in the mixed solution with use of such a dipolar aprotic solvent, it is preferred to keep the reaction system in a dry atmosphere by removing water therefrom. That is, the reaction intermediate represented by the above formula (Ib), i.e. the C-terminal carboxy group being activated by converting into an asymmetric acid anhydride, undergoes hydrolysis when water molecules come into the reaction system, and returns to the original carboxy group. In order to avoid such a deactivation process, the reaction system is preferably maintained in a water-removed state.

For example, the sulfur, which is present on methionine included in the amino acid residues constituting a target peptide, may undergo oxidation by the oxygen incoming into the system and change its formula weight. Prevention of, this oxidation by oxygen is further preferred in the method of the present invention, which is based on the measurement of molecular weights, in order to achieve a higher accuracy.

Incidentally, for instance, when a target peptide contains cysteine that forms an oxidized type —S—S— bond between the cysteines of two adjacent molecules or contains a —S—S— bond formed within the molecule, an ordinary reducing treatment is conducted beforehand to break off such bridging, and thereby the peptide is converted into a peptide containing reduced type cysteine(s). Further in many cases, to the reduced type cysteine(s) present in a target peptide to be analyzed, there is beforehand applied, to the sulfanyl group (—SH) on the side chain thereof, carboxymethylation, pyridylethylation, or the like for protection thereof. Meanwhile, when no protection is beforehand made to the reduced type cysteine(s), there is a fear that the cysteine(s) undergoes oxidation by the oxygen contaminating in the system and the oxidized type —S—S— bond may be occasionally reformed thereby. In the present invention, there is used a peptide from which a structure of higher order has been dissolved out beforehand as a target peptide; however, in order to avoid the formation of unneeded —S—S— bond between adjacent peptides, the reaction system is desired to be kept in a dry atmosphere where not only water but also oxygen is removed, in the course of said reaction treatment in the mixed solution using a dipolar aprotic solvent. Also, in order to prevent oxidation of the sulfide (—S—) of methionine residue, the system is desired to be maintained in such a dry atmosphere from which oxygen is also removed away.

As for means for keeping the reaction system in a dry atmosphere where not only water but also oxygen is removed, it is desired to, for example, keep the system for the reaction in a sealed state to prevent the incoming of water and oxygen from outside, and to further conduct operations for the introduction and discharge of liquid in a inert gas (e.g. nitrogen) atmosphere being treated for drying-up.

In the process for selective release of C-terminal amino acids according to the present invention, it is understood that, from the once-formed 5-oxazolone ring, the separation of the C-terminal amino acid and the formation of the reaction intermediate for the next stage proceed, for instance, via such a reaction as shown by the following reaction scheme (II'):

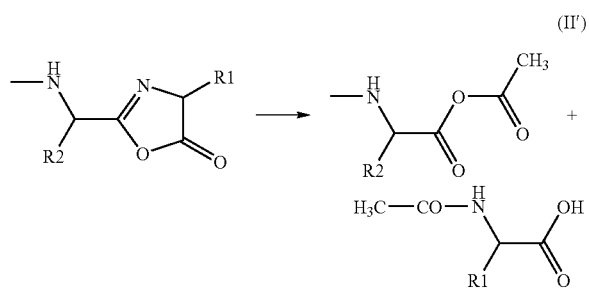

as a result, successive release of C-terminal amino acids is advanced in such a way. Therefore, the reaction products obtained after the completion of such reactions are a mixture comprising, in addition to those having a carboxy group exposed at the C-terminus, such as shown in the above reaction scheme (II), an intermediate product having the 5-oxazolone ring structure, or a form of reaction intermediate in which its C-terminus has been converted into the form of asymmetric acid anhydride.

The successive reaction occurring in the step of selectively releasing the C-terminal amino acids is constructed at least at least two-stage elementary reactions, i.e. a stage of formation of 5-oxazolone ring structure as illustrated by the reaction scheme (Ib) and a stage of separation of C-terminal amino acid by the cleavage of 5-oxazolone ring structure, as illustrated by the reaction scheme (II'). Therefore, the overall reaction rate depends upon the reaction rates of the two stages, but depends mainly upon the concentrations of the alkanoic acid anhydride and perfluoroalkanoic acid used as well as on the reaction temperature. In addition, since a series of reaction products are formed by successive reactions, the maximum length of C-terminal amino acid sequence removed by such successive reactions becomes longer as the treatment duration becomes longer. Hence, the treatment duration for the step of successively releasing C-terminal amino acids needs to be appropriately chosen depending mainly upon the concentrations of the alkanoic acid anhydride and perfluoroalkanoic acid used and the reaction temperature employed and also in view of the intended length of the C-terminal amino acid sequence to be analyzed.

The termination of the reaction for successive release of selected C-terminal amino acids is conducted by lowering the temperature of the reaction system and removing the reaction reagent infiltrated into the gel carrier, i.e. the perfluoroalkanoic acid and the alkanoic acid anhydride by dilution. Specifically explaining, the termination of the reaction for release and the removal of the reaction reagent are conducted by diluting and removing the mixed solution used for the reaction for successive release of C-terminal amino acids, with a polar aprotic solvent which causes no dissolution of the gel substance and has affinity for the perfluoroalkanoic acid and the alkanoic acid anhydride as well as the dipolar aprotic solvent. The dilution and removal of the reaction reagent may be conducted by using the dipolar aprotic solvent used for preparation of the mixed solution. However, for termination of the formation of 5-oxazolone ring structure such as illustrated by the reaction scheme (Ib), it is more desirable to employ such a step of removing the perfluoroalkanoic acid and the alkanoic acid as well as the dipolar aprotic solvent by using a polar aprotic solvent which makes little contribution to stabilization of the intermediate of enol type. At least in the final stage of the dilution and removal of the reaction reagent, there is employed treatment for dilution and removal using a polar aprotic solvent. When, for example, a polyacrylamide gel is used, there can be mentioned, as for the polar aprotic solvent satisfying these requirements, nitrites having 4 or less carbon atoms such as acetonitrile ($CH_3CN$) and ketones having 4 or less carbon atoms such as acetone can be exemplified.

In addition, the process of the present invention can comprise a further step for hydrolysis treatment in order to convert even the product being in the form of such reaction intermediate as illustrated in the reaction scheme (II'), which has no exposed carboxy group at the C-terminus and is formed in the step of successive treatment for selective release of the C-terminal amino acids, into a form having an exposed carboxy group at the C-terminus. That is, the present process is preferred to comprise additional step for hydrolysis treatment and then redehydration treatment, in which step the hydrolysis treatment for said mixture comprising a series of reaction products obtained by the reaction for successive release of C-terminal amino acids is conducted by immersing the gel carrier in an aqueous solution dissolving a basic nitrogen-containing aromatic compound or a tertiary amine compound therein to allow a water molecule to act, in the presence of said basic nitrogen-containing organic compound, on said peptides of the reaction products being still bound on the gel carrier; and then, the redehydration treatment for the gel carrier is performed by removing said aqueous solution infiltrated into the gel carrier by dilution with use of a polar aprotic solvent having no solvency for the gel substance and having affinity for water. By applying this post-treatment, the reaction products come to take a form having an exposed carboxy group at the C-terminus; after that, the products of such a form give main peaks when analyzed by mass spectrometry; which will make it easier to carry out operation for identifying these peaks showing the molecular weights which is corresponding to a series of reaction products by referring to the intensities thereof.

In said additional treatment for hydrolysis, the basic nitrogen-containing aromatic compound or tertiary amine compound catalyses the reaction of hydrolysis of the 5-oxazolone ring structure shown in the reaction scheme (II') and the reaction intermediate for the next-stage (acid anhydride form); indeed, the compound per se does not react with the 5-oxazolone ring structure or the reaction intermediate (acid anhydride form) to produce an undesired by-product but functions as an appropriate base catalyst. Specifically explaining, in the reaction for hydrolysis of the 5-oxazolone ring structure and the next-stage reaction intermediate (acid anhydride form) shown in the reaction scheme (II'), an the carboxy group is exposed at the C-terminus of peptide chain of the reaction products, as shown in the following reaction scheme (IV).

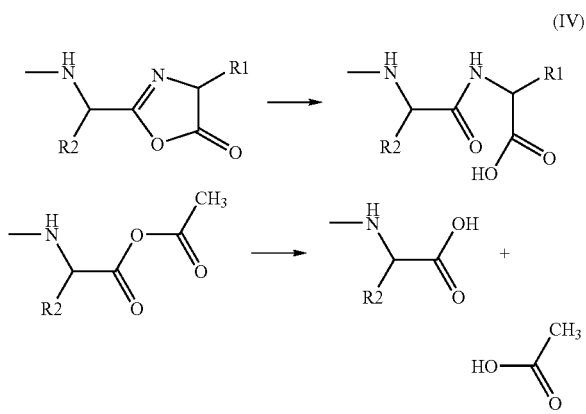

Incidentally, when there remains the basic nitrogen-containing aromatic compound or tertiary amine compound used for the hydrolysis treatment, it happens to incorporate as an adduct salt that is formed by binding of the nitrogen base to the carboxy group exposed at the C-terminus of each reaction product. Therefore, it is preferred that the aqueous solution included in the gel carrier is removed by dilution using a polar aprotic solvent which causes no dissolution of the gel substance and has affinity for water and, thereby, the gel carrier is redehydrated and the basic nitrogen-containing aromatic compound or tertiary amine compound used for the hydrolysis treatment as well as the water are removed by dilution. Accordingly, the polar aprotic solvent used in the step for redehydration treatment is more preferably one having high solvency even for the basic nitrogen-containing aromatic compound or tertiary amine compound. When, for example, a polyacrylamide gel is used, there can be exemplified, as the polar aprotic solvent for redehydration, satisfying these requirements, nitriles having 4 or less carbon atoms such as acetonitrile ($CH_3CN$) and ketones having 4 or less carbon atoms such as acetone.

The aforementioned basic nitrogen-containing aromatic compound or tertiary amine compound used for the hydrolysis treatment is a preferred compound because it does not react with, for example, the remaining reaction intermediate whose C-terminus has been converted into an asymmetric acid anhydride, to form an amide bond and further, when made into an aqueous solution, can become a uniform solution. As the basic nitrogen-containing aromatic compound being usable, preferred is a monocyclic, nitrogen-containing aromatic compound that exhibits high solubility in polar aprotic solvents and, for instance, pyridine is more suitably employed. As the tertiary amine compound being usable, preferred is a compound showing the equivalent basicity to said relatively weak basicity which pyridine exhibits and, for example, DMAE [2-(dimethylamino)ethanol, $(CH_3)_2N-CH_2CH_2OH$] is more suitably employed. When, for example, pyridine is used, the amount of pyridine is preferably selected in a range of 5 to 15% by volume relative to the whole volume of the aqueous solution, more particularly at 10% by volume. On the other hand, when DMAE is used, the amount of DMAE is preferably selected in a range of 1 to 20% by volume relative to the whole volume of the aqueous solution, more particularly at 10% by volume.

The monocyclic, nitrogen-containing aromatic compound or tertiary amine compound is allowed to act on the gel on which the reaction products are bound, in the form of an aqueous solution. In this post-treatment, the aqueous solution containing such an organic base infiltrates quickly into the highly hydrophilic gel substance. The reaction temperature is selected preferably at 60° C. or above for quick completion of the hydrolysis. However, since the reaction is conducted in a tight-sealed reactor, the reaction temperature is desirably selected generally at 100° C. or below, in view of the mechanical strength of the reactor.

In addition, after the reaction for successive release of C-terminal amino acids, said hydrolysis treatment can be conducted after the completion of the operation for dilution and removal of the alkanoic acid anhydride and the perfluoroalkanoic acid used as the reaction reagents by using the polar aprotic solvent. Alternatively, the reaction for successive release of C-terminal amino acids and the hydrolysis treatment may be carried out continuously. Specifically explaining, when the aqueous solution containing the organic base is added while the reaction temperature is cooled down to terminate the reaction for successive release of C-terminal amino acids, there occur the deactivation of the reaction reagent, which comprises a combination of the alkanoic acid anhydride and the perfluoroalkanoic acid, and its elusion out from the gel; which gives rise to the termination of the reaction for successive release of C-terminal amino acids and the deactivation and removal of the reaction reagent. Successively, the hydrolysis treatment of reaction products can be made and, by finally performing the step of redehydration treatment using a polar aprotic solvent, there take place removal of the alkanoic acid that is derived from the alkanoic acid anhydride, the perfluoroalkanoic acid and the dipolar aprotic solvent which are well mixed in the aqueous solution of organic base, as well as redehydration; therefore, there is substantially no difference from the case in which the operation for washing and removal using a polar aprotic solvent is beforehand employed in the middle.

In addition to the treatment step using said mixed solution of an alkanoic acid anhydride added with a small amount of a perfluoroalkanoic acid in relative ratio thereto, the process for successive release of C-terminal amino acids according to the present invention can further comprise, prior to said step of successively releasing C-terminal amino acids, a pretreatment step of applying, to the N-terminal amino group of target peptide, N-acylation protection by the acyl group derived from the alkanoic acid that composes said alkanoic acid anhydride. Specifically explaining, in the stage of treatment using said mixture of an alkanoic acid anhydride added with a small amount of a perfluoroalkanoic acid in relative ratio thereto, a reaction intermediate in which the C-terminal carboxy group of peptide is activated is presumed to be formed; when this reaction intermediate reacts with the N-terminal amino group of an adjacent peptide to form an amide bond, whereby no intended reaction product of which peptide is truncated is obtained; since the reaction for formation of such a reaction intermediate takes place to the peptide bound in the porous structure of gel substance; it is desired to apply N-acylation protection beforehand, although the frequency of said accidental side reaction arising between a plurality of reaction intermediates of peptide is not high.

In the course of the treatment using the mixed solution of an alkanoic acid anhydride added with a small amount of a perfluoroalkanoic acid in relative ratio thereto, the N-terminal amino group of peptide ordinarily undergoes N-acylation by the alkanoic acid anhydride and, consequently, N-acylation protection takes place in the system; however, it is more desirable to apply the above-mentioned pretreatment step of N-acylation protection beforehand.

Since this pretreatment step of applying N-acylation protection to the N-terminal amino group is conducted through the reaction by using an alkanoic acid anhydride, the step is desirably carried out in a state that no water remains in the gel substance. Therefore, this pretreatment step of applying N-acylation protection is provided after the step of dehydration treatment for removing water included in the gel substance and prior to the step of successive release of C-terminal amino acids. The alkanoic acid anhydride is dissolved in the same dipolar aprotic solvent to that used for preparation of said mixed solution of the alkanoic acid anhydride added with a small amount of the perfluoroalkanoic acid in relative ratio thereto; in the resulting solution is immersed the dehydrated gel carrier; thereby, there take place swelling of gel and infiltration of the solution into gel substance.

In the dipolar aprotic solvent, the intramolecular polarization within the alkanoic acid anhydride is induced thereby, and it acts on the amino group of peptide as an electrophilic reaction reagent; whereby, N-acylation proceeds sufficiently even at a temperature of 30° C. or higher. The reaction temperature is preferred in general to be selected at 50° C. or above to achieve promotion of the reaction; however, since the reaction is conducted in a sealed reactor, the reaction temperature is commonly desired to be selected in a range of 100° C. or below, in view of the mechanical strength of the reactor. An alkanoic acid is formed in association with the N-acylation; however, its amount is slight and the side reaction caused by the proton donatability of such an alkanoic acid and the co-existing alkanoic acid anhydride poses no problem ordinarily in the above-mentioned temperature range. Specifically explaining, the alkanoic acid formed within the system, as compared with, for example, the perfluoroalkanoic acid, is far inferior in effect of acid catalysis and small in amount; therefore, under the above-mentioned temperature condition, there occurs coincidentally no initiation for the reaction of 5-oxazolone ring structure formation which is a main reaction used in the step of successive release of C-terminal amino acids with use of a perfluoroalkanoic acid and an alkanoic acid anhydride. Further, in the pretreatment step using only an alkanoic acid anhydride, various side reactions, e.g. cleavage of amide bond (—CONH—) of peptide main chain, which are suppressed even in the step of successive release of C-terminal amino acids using a perfluoroalkanoic acid and an alkanoic acid anhydride, are suppressed more strongly.

In addition, in applying N-acylation protection to the N-terminal amino group of peptide, N-acylation protection takes place simultaneously even at amino group on the side chain of each lysine residue that is present in the target peptide. Further, O-acylation reaction takes place at the hydroxy groups on the side chain of each serine residue and threonine reside present in the target peptide, whereby the protection thereof is also made. Furthermore, O-acylation reaction takes place partially at the phenolic hydroxy group on the side chain of the tyrosine residue present in the target peptide, of which reactivity for this O-acylation is different from those of serine and threonine. As a result of adding the pretreatment step in which such acylation protections for plurality of amino acids take place, the amino group on the side chain of lysine residue and the hydroxy groups on the side chains of serine residue and threonine residue are all acylated and become unable to take part in undesirable side reactions. From this standpoint as well, it is preferred ordinarily to carry out the pretreatment step of applying N-acylation protection to the N-terminal amino group of the target peptide.

When the vapor of the perfluoroalkanoic acid is allowed to act on a dried peptide chain at, for example, 90° C. in the presence of water vapor, such a side reaction may occur at the serine residue [—NH—CH($CH_2$OH)—CO—] in the peptide chain, in which a N,O-acyl rearrangement reaction between the α-position amino group (—NH—) and the β-position hydroxy group (—OH) is progressed; successively, hydrolysis takes place, and thereby peptide cleavage takes place at the N-terminal side of serine residue. Further, depending upon the condition, such a side reaction may occur at the threonine residue [—NH—CH(CH($CH_3$)OH)—CO—] having a hydroxy group (—OH) at the β-position, in which hydrolysis is progressed through the same reaction mechanism; and thereby peptide cleavage takes place at the N-terminal side of threonine residue. Furthermore, at the aspartic acid residue [—NH—CH($CH_2$COOH)—CO—] in the peptide chain, such a side reaction may occur in which the rearrangement of peptide bond from C-terminal carboxy group to β-position carboxy group and subsequent hydrolysis take place, and thereby peptide cleavage takes place at the C-terminus of aspartic acid residue.

When peptide cleavage is caused by these side reactions, successive release of C-terminal amino acids takes place simultaneously also to the N-terminal side peptide fragments resulted therefrom. If reaction products from these side reactions co-exist, they may be occasionally factors to interfere the measurement for the mass spectrometry analysis of intended reaction products.

Further, even if no peptide cleavage takes place, if there is formed a branched peptide in which N-terminal side partial peptide is bonded to the β-position hydroxy group (—OH), amide bond is lost at the site, there occurs no formation of oxazolone ring structure, whereby further progress in successive release of C-terminal amino acids will be hindered.

In the step of successive release of C-terminal amino acids in the present method, the step of dehydration treatment is provided to remove the water in gel beforehand; and such a condition is selected that no water will income into the reaction system, the reaction is carried out with the content of perfluoroalkanoic acid being suppressed low at a catalytic amount; as a result, there are suppressed the above-mentioned side reactions such as peptide cleavage at the particular amino acid residues and formation of branched peptide. In addition, since there also proceed simultaneously the N-acylation protection and O-acylation protection by the alkanoic acid anhydride which is present in a far higher concentration than the perfluoroalkanoic acid, the side reactions such as peptide cleavage and formation of branched peptide are further suppressed and avoided. However, if the pretreatment step using the alkanoic acid anhydride is carried out beforehand under the condition that no perfluoroalkanoic acid co-exists therein, in addition to N-acylation protection for the N-terminal amino group of peptide, acylation protections for the amino group and hydroxy group on the side chain of peptide take also place; as a result, side reactions such as peptide cleavage and formation of branched peptide in the step of the successive release of C-terminal amino acids can be suppressed and avoided more reliably.

Incidentally, the content of alkanoic acid anhydride in the solution of alkanoic acid anhydride dissolved in dipolar aprotic solvent, which is used for the pretreatment step, can be selected so as to achieve an intended reactivity, depending upon the reaction temperature; however, the content of alkanoic acid anhydride in dipolar aprotic solvent is preferred to be selected in a range of 10 % to 30% by volume, for instance, at about 10% by volume. At such a content of alkanoic acid anhydride, the reaction temperature is preferred to be chosen in a range of 30° C. to 80° C., preferably in a range of 50° C. to 80° C., more preferably at around room temperature or at a temperature slightly higher than room temperature, more particularly in a range of 50° C. to 60° C. The reaction time is dependent upon the reaction temperature and the content of alkanoic acid anhydride in dipolar aprotic solvent, and moreover, taking also the time needed for the swelling of the gel carrier shrunk in association with the dehydration treatment using a polar aprotic solvent into consideration, it is appropriately chosen.

After the pretreatment step, it is desired to remove the solution (used in the step) of alkanoic acid anhydride dissolved in dipolar aprotic solvent and further dilute and remove the alkanoic acid anhydride, dipolar aprotic solvent, and formed alkanoic acid infiltrated into the gel, using the same polar aprotic solvent as used in the dehydration step. That is, in a state that the solution of alkanoic acid anhydride has been infiltrated into the gel, there is no rapid infiltration of perfluoroalkanoic acid into gel when, in the next step of successive release of C-terminal amino acids, the gel carrier is immersed in a mixed solution containing an alkanoic acid anhydride and a small amount of a perfluoroalkanoic acid; in order to reliably promote the feeding of perfluoroalkanoic acid into gel, it is desired to once dilute and remove the alkanoic acid anhydride solution infiltrated into the gel, using the same polar aprotic solvent as used in the dehydration step.

On the other hand, at the operation for the termination of reaction and removal of reaction reagent in the pretreatment step of N-acylation protection, there may be used, in place of the method of conducting dilution and washing using a polar aprotic solvent, a way for conducting termination of reaction and removal of reaction reagent, which comprises cooling down the temperature to stop the disociation reaction and then adding water for the inactivation of alkanoic acid anhydride used as reaction reagent and the elution out of alkanoic acid anhydride and corresponding alkanoic acid present in gel. After this reaction termination using water, it is necessary to once dilute and remove the added water using the same polar aprotic solvent as used in the dehydration step, to dehydrate the gel. That is, since remaining of water in gel carrier hinders the successive release of C-terminal amino acids, sufficient rinsing and washing is carried out using the same polar aprotic solvent as used in the dehydration step for gel carrier after gel electrophoresis.

It is highly preferable that the process for successive release of C-terminal amino acids according to the present invention is carried out, for instance, in such a mode comprising all of the dehydration step, the pretreatment step, the step of successive release of C-terminal amino acids and the post-treatment step. In this case, in a stage before completion of each of the pretreatment step, the step of successive release of C-terminal amino acids and the post-treatment step, the reaction reagent used in the step is removed from inside the gel to terminate the reaction of the step; therefore, as described above, dilution and washing is conducted using the same polar aprotic solvent as used in the dehydration step. After this dilution and washing using the polar aprotic solvent and before the start of the next step, the gel carrier may be stored temporarily in a state that is immersed in the polar aprotic solvent. Alternatively, the gel carrier may be stored temporarily in a state that the polar aprotic solvent has been vaporized and removed and the gel carrier has been dried.

In the method for analysis of the C-terminal amino acids of peptide according to the present invention., there are determined the molecular weights of the series of reaction products prepared by successive release of C-terminal amino acids and the molecular weight of the original peptide by using the measurements by mass spectrometry, and there are identified amino acids based on the differences between the above-obtained molecular weights. Therefore, it is generally desired that the original peptide remains in the mixture subjected to the measurement by mass spectrometry, in such an amount as to enable the measurement of its molecular weight.

Specifically explaining, the method for analysis of the C-terminal amino acid sequence of peptide according to the present invention is applied to such a case where the maximum amino acid length analyzed for the C-terminal amino acid sequence is about ten odd amino acids. With respect to the contents of corresponding series of reaction products whose maximum kinds are ten and odd, the content of the minimum content reaction product is desired to be at least not smaller than about $1/10$ of the content of the maximum content reaction product. In addition, the remaining amount of the original peptide as well is desired to be at least not smaller than about $1/10$ of the content of the maximum content reaction product. Meanwhile, the information of C-terminal amino acid sequence is required for 10 or less amino acids in many cases and, when there is selected a treatment time in which about 10 amino acids are released, the above-mentioned requirements regarding the contents can be satisfied.

On the other hand, Mass spectrometry is used for the measurement of molecular weight. There is suitably used a mass spectrometry apparatus which can conduct ionization in such a condition that can suppress fragmentation, i.e. the partial detachment of atomic group from amino acid residues constituting the target peptide. Since the target peptide, etc. are high-molecular compounds, there is also preferably used a mass spectrometry apparatus suitable for the measurement of such a high-molecular weight compound, for example, a. MALDI-TOF MS apparatus. In the present method for analysis of the C-terminal amino acid sequence of peptide, the peptide sample to be analyzed is beforehand separated by gel electrophoresis and is subjected to a series of treatments in a state bound on the gel carrier used; and the reaction products after these treatments are selectively isolated and recovered from the spot on the gel carrier and subjected to mass spectrometry. In this case, in particular, it is preferred to use, for example, a MALDI-TF-MS apparatus which can measure both cationic species and anionic species, corresponding to each other.

However, even when there is used such a mass spectrometry apparatus, there is an upper limit as to the molecular weight allowing for effective ionization and, therefore, it is desired that the maximum amino length of a peptide that is subjectable to measurement, does not exceed 30 to 50 amino acids. In addition, corresponding amino acids are identified based on the measured differences in molecular weight; therefore, in order to distinguish two amino acid residues giving a formula weight difference of 1, such as Asn vs Asp, or Gln vs Glu, from each other at a high precision, the molecular weight of the longest peptide, i.e. the peptide with no release of C-terminal amino acid therefrom that is used as a datum point, is preferably in a range of no more than 3,000, more preferably in a range of no more than 2,000. When the molecular weight is reduced to an amino acid length, the length is preferably 30 amino acids at longest, more preferably in a range of no more than 20 amino acids.

When the method for analysis of the C-terminal amino acid sequence of peptide according to the present invention is applied to a peptide having an amino acid length far larger than the above-mentioned amino acid length, e.g. a protein, it is desired that, prior to carrying out mass spectrometry, cleavage of peptide at particular sites is conducted using, for example, a protease having specificity for the cleavage sites of amino acid sequence, to allow the C-terminal peptide fragments obtained to have the above-mentioned amino acid length. That is, when the original peptide and a series of reaction products prepared undergo cleavage at the particular sites, the C-terminal peptide fragments obtained are a series of peptide fragments having the same N-terminal amino acid and a different C-terminal amino acid portion. By measuring the molecular weights of a mixture of the series of peptide fragments by mass spectrometry, the method for analysis of the C-terminal amino acid sequence of peptide according to the present invention can be utilized.

Thus, in the present invention, when subjected to cleavage at the particular sites, the fragments resulted can be eluted out from the gel carrier, but the reaction products themselves obtained by successive release of C-terminal amino acids need to remain on the gel carrier used; in particular, the original peptide before successive release of C-terminal amino acids needs to have specifically at least 50 amino acid residues, ordinarily 100 or more amino acid residues.

The cleavage of peptide at particular sites using, for example, a protease having specificity for the cleavage sites of amino acid sequence is carried out ordinarily after the post-treatment of hydrolysis. Specifically explaining, there is conducted, after the post-treatment, dilution, washing and a dehydration treatment using a polar aprotic solvent, after which an aqueous solution containing the above-mentioned protease is allowed to act on the peptide chains bound on gel carrier. In this case, the peptide chains bound on gel carrier undergo cleavage at the particular sites of each amino acid sequence by the action of the peptide penetrating into the porous structure of the gel, and each peptide chain becomes a plurality of peptide fragments. As the protease for cleavage of peptide and fragmentization thereof on gel carrier, there can be used proteases widely used for peptide fragmentization, such as trypsin (capable of cleaving the C-terminal side peptide bond of lysine and arginine residues), V8 enzyme (capable of cleaving the C-terminal side peptide bond of glutamic acid residue) and the like.

The cleave of peptide at the particular sites can be conducted not only by using a protease having specificity for the cleavage sites of amino acid sequence, but also by using a chemical reagent, for example, CNBr having specificity for cleavage of the C-terminal side amide bond of methionine reside.

In order to allow the C-terminal side peptide fragments obtained from a peptide chain of large amino acid length by the above-mentioned protease cleavage or chemical cleavage, to have a desired amino acid length, it is desired that there are present, in the peptide chain before cleavage, to-be-cleaved sites of, for example, 10 to 2, preferably 7 to 2 per 100 amino acids. When there are to-be-cleaved sites of such a number, the average amino acid length of the resulting peptide fragments can be 10 to 50 amino acids, preferably 15 to 35 amino acids and, in association therewith, the C-terminal side peptide fragments also can have the above-mentioned amino acid length range. Thus, it becomes possible to prepare C-terminal side peptide fragments having a molecular weight range preferred in the molecular weight measurement using, for example, a MALDI-TOF-MS apparatus. In this respect, it is desired that, in using trypsin for cleavage of the C-terminal side peptide bond of lysine residue or arginine residue, N-acylation protection is made to the side chain amino group of lysine residue, only the C-terminal side peptide bond of arginine residue is cleaved and, thereby, the number of to-be-cleaved sites is adjusted.

Each peptide chain bound on the gel carrier used is held in the porous structure of the gel owing to its large amino acid length; however, when the peptide chain is subjected to fragmentization, peptide fragments of smaller amino acid length can be isolated easily from the gel carrier and dissolved in, for example, the protease solution used. The peptide fragments that are eluted from the gel carrier in association with said treatment of fragmentization are recovered. Then, a desalting treatment or the like is conducted to separate the peptide fragments from the component contained in the buffer solution used, to obtain crude peptide fragments, which are dried and recovered.

When the process of the present invention is applied to a long peptide such as a protein being constructed in a tertiary structure and when there is, in the long peptide, a —S—S— bond formed between cysteine resides owing to the folding of protein, it is necessary to beforehand reduce such a —S—S— bond and eliminate the bridging between the cysteine residues; in addition, modification such as carboxymethylation or the like is made to the reduced cysteines to protect the side chain sulfanyl group (—SH). In addition, at the portions constituting a secondary structure (e.g. α-helix) formed by the folding of protein, the carbonyl group (C=O) and imino group (—NH—) constituting the amide bond of amino acid residue forms a hydrogen bond in the molecule. When this hydrogen bond is maintained in the molecule, the reactions conducted in the present invention may be suppressed. In view of this matter, it is desired that at least the C-terminal portion of peptide is put in a state in which no secondary structure has been formed, for example, a state in which a defolding treatment has been applied, and the resulting peptide sample is subjected to gel electrophoresis such as two-dimensional electrophoresis, SDS-PAGE method or the like to obtain a single spot on the gel carrier used. In addition, by putting in a state in which a defolding treatment has been applied, there is an advantage that, even when cleavage of peptide at the particular sites using a protease or the like is necessary after a series of chemical treatments but prior to mass spectrometry, separation of the resulting C-terminal peptide fragments is easy generally.

The method for analysis of the C-terminal amino acid sequence of peptide according to the present invention is applicable not only for determination of the C-terminal amino acid sequence of chain peptide, but also for determination of the C-terminal amino acid sequence of cyclic peptide by opening of the cyclic peptide and conversion into chain peptide. Specifically explaining, various microorganisms, for example, produce cyclic peptide type compounds having a biological activity and the present method is applicable for determination of the partial amino acid sequences of such compounds. Further, in some proteins, a plurality of peptide chains form a —S—S— bond between cysteine residues; for such a case, the present analysis method is applicable by reducing the —S—S— bond to eliminate the bridging between cysteine residues, subjecting the resulting individual peptide chains to gel electrophoresis to separate them as individual spots (individual peptides), and analyzing the C-terminal amino acid sequence of each peptide.

Therefore, in applying the present method, the peptide to be analyzed, is converted into a chain peptide and subjected to gel electrophoresis to obtain as a single spot bound on the gel carrier used. As the gel electrophoresis, there may be used not only a conventional SDS-PAGE method (a one-dimensional method) but also a two-dimensional migration method of conducting two-dimensional migration on a gel for higher-degree separation. A peptide sample separated by such a two-dimensional migration method contains no impurity and, even when its sample amount is very small, its C-terminal amino acid sequence can be determined by the method of the present invention for analysis of the C-terminal amino acid sequence of peptide. In peptide separation by gel electrophoresis, when the target peptide has, in the molecule, a —S—S— bond formed between cysteine residues, it is preferred to add a reducing reagent such as 2-sulfanylethanol (HS—$C_2H_4$—OH, 2-mercaptoethanol), DTT (dithiothreitol, threo-1,4-disulfanyl-2,3-butanediol) or the like, and conduct electrophoresis in a reduced state for separation as a single spot. Or, it is preferred to reduce the —S—S— bond formed between cysteine residues in the molecule and apply, to the reduced cysteines, modification such as carboxymethylation using iodoacetic acid or the like, for separation as a single spot.

In the method of the present invention for analysis of the C-terminal amino acid sequence of peptide, since the C-terminal amino acids successively released are identified based on the differences in molecular weight, it is difficult in principle to make distinction between leucine (Leu) residue and isoleucine (Ile) residue both having the same formula weight, and this is the same as in the conventional technique for analysis of C-terminal amino acid sequence using mass spectrometry. In the reaction for release of C-terminal amino acid, it is requisite, as illustrated in the reaction formula (Ib), to convert the amide bond into enol form and subsequently form a 5-oxazolone ring structure; therefore, the reaction for release does not proceed any further at a timing when the C-terminal amino acid has become a cyclic amino acid, proline (Pro) containing neither carbonyl group (C=O) nor imino group (—NH—) both necessary for formation of amide bond. In other words, when the treatment time has been extended and no further release of C-terminal amino acid has been confirmed, the amino acid residue causing it can be presumed to be a cyclic amino acid, proline (Pro).

By the aforementioned treatment for peptide fragmentization on a gel carrier using a protease, there are produced C-terminal fragments derived from a series of reaction products obtained by successive release of C-terminal amino acids as well as other intermediate portions of peptide chains and fragments derived from N-terminal side. Then, by measuring the molecular weights thereof, there can be identified additional features in related to the amino acid sequence of the original peptide chain, such as intervals of the positions of specific sites for cleavage by protease, which are present in the original peptide chain, and the presence of the specific amino acids sequence of the cleavage site for said protease at the N-terminus of each C-terminal fragment.

In the present method, in the pretreatment step for N-acylation protection of the N-terminal amino group of peptide and the step for successive release of C-terminal amino acids, there occur N-alkanoylation of N-terminal amino group; N-alkanoylation of ε-position amino group of lysine residue [—NH—CH($CH_2CH_2CH_2CH_2NH_2$)—CO—]; O-alkanoylation of hydroxy groups of serine residue [—NH—CH($CH_2OH$)—CO—] and threonine residue [—NH—CH(CH($CH_3$)OH)—CO—]; and O-alkanoylation of phenolic hydroxy group of tyrosine residue [—NH—CH($CH_2$—$C_6H_4$—OH)—CO—]. In the post-treatment step, i.e. the hydrolysis treatment in the presence of an organic nitrogen base, the ester bonds to alcohol type hydroxy groups are hydrolyzed more quickly than the ester bond to phenol type hydroxy group. As a result, in the final reaction products after the post-treatment step, there remain, at a higher selectivity, only N-alkanoylation of N-terminal amino group; N-alkanoylation of ε-position amino group of lysine residue [—NH—CH($CH_2CH_2CH_2CH_2NH_2$)—CO—]; and, in some cases, O-alkanoylation of phenolic hydroxy group of tyrosine residue [—NH—CH($CH_2$—$C_6H_4$—OH)—CO—].

If a number of acetylated forms of serine residue and threonine residue are included in the reaction products obtained finally, the molecular weight differences between such multi-acetylated product and deacetylated product are aligned in the integral times of formula weight 42, specifically 84, 126 and 168, and they are close to the formula weight 87 of serine residue [—NH—CH($CH_2OH$)—CO—], the formula weight 128 of glutamine residue [—NH—CH($CH_2CH_2$—$CONH_2$)—CO—], the formula weight 129 of glutamic acid residue [—NH—CH($CH_2CH_2$—COOH)—CO—] and the formula weight 170 of N-acetyllysine residue [—NH—CH($CH_2CH_2CH_2CH_2NH$—$COCH_3$)—CO—], respectively. Therefore, there is some fear that the peaks for the multi-acetylated products may be mistaken as main peaks and the deacetylated products may be regarded as the above-mentioned amino-acid-eliminated products. In the present method, the measurement is actually made at such an accuracy as to enable distinction between glutamine residue and glutamic acid residue of which difference in formula weight is only 1, and said differences in formula weight are 2 to 3 between those for the difference in the residual acetyl group number and those for the amino acid residues showing a similar formula weight; therefore, the possibility for the occasion of the aforementioned mis-assignment is not high in many cases. When these are taken into consideration, it is more preferable to apply the above-mentioned post-treatment in other to eliminate the undesired remaining of alkanoyl groups.

EXAMPLES

The present invention is described specifically below by way of Examples. These Examples are examples of the best mode for carrying out the present invention; however, the present invention is in no way restricted by such examples.

Example 1

In order to verify the usefulness of the method for analysis of the C-terminal amino acid sequence of peptide according to the present invention, analysis of C-terminal amino acid sequence was conducted for globin peptide chain, a protein portion of the horse myoglobin which is a heme protein comprising 153 amino acids.

The amino acid sequence possessed by the globin peptide chain of the horse myoglobin which is a sample to be analyzed in this Example, is already known. Using this sample, the accuracy of the analysis of C-terminal amino acid sequence according to the method of the present invention was verified.

(Isolation by Means of Gel Electrophoresis)

First, a commercially available horse myoglobin standard product is made into a peptide solution containing only the globin peptide chain portion thereof at a concentration of 0.2 μg/μl. Incidentally, the globin peptide chain portion of horse myoglobin contains no cysteine residue unlike human myoglobin; however, if there is used a peptide containing cysteine residue, like human myoglobin, an anti-oxidation treatment is applied beforehand in order to avoid the oxidation of the sulfanyl group (—SH) of the cysteine residue and subsequent formation of —S—S— bond, by, for example, adding a reducing reagent such as 2-sulfanylethanol, DTT or the like.

This peptide solution is spotted on a polyacrylamide gel of gel concentration 12.5% by mass, followed by electrophoresis. Then, Coomassie staining was conducted to identify a band of intended globin peptide chain. In this Example, the stained band portion of gel is cut out and the resulting gel slice is used for a series of operations described below.

(Dehydration Treatment of Gel)

The gel slice is placed in an air-tight tube; 1 ml of acetonitrile is poured thereinto; stirring is made for 15 minutes. Then, the acetonitrile is discarded; 1 ml of acetonitrile is added newly; stirring is made again for 15 minutes. This extraction of water in gel by acetonitrile is conducted three times in total to dehydrate the gel. With the dehydration, the gel volume contracts.

(Pre-Treatment Operation)

Next, to the dehydrated gel slice in the tube is added 1 ml of a formamide solution containing 10% by volume of acetic anhydride. The whole tube is sealed and held at 50° C. for 3 hours in a dry atmosphere with stirring.

During this period, the gel in contraction reswells owing to the infiltration of formamide solvent and returns to its original volume. The globin peptide chain carried on the reswollen gel undergoes the action of acetic anhydride solute at the above temperature. As a result, there proceeds selective acetylation of the N-terminal amino group of the peptide. In addition, there take place N-acetylation of the ε-position amino group of the lysine residue [—NH—CH(CH$_2$CH$_2$CH$_2$CH$_2$NH$_2$)—CO—]contained in the peptide chain; O-acetylation of the hydroxy groups present in the serine residue [—NH—CH (CH$_2$OH)—CO—] and the threonine reside [—NH—CH (CH$_3$)OH)—CO—]; and O-acetylation of the phenolic hydroxy group of the tyrosine residue [—NH—CH(CH$_2$—C$_6$H$_4$—OH)—CO—].

After the above-mentioned N-acetylation of N-terminal amino group and N-acetylation/O-acetylations of side chains of amino acid residues, the formamide solution of acetic anhydride is removed; 1 ml of acetonitrile is poured into the tube; stirring is conducted for 15 minutes. Then, the acetonitrile is discarded; 1 ml of acetonitrile is added newly; stirring is made again for 15 minutes. This extraction of formamide solution in gel by acetonitrile is conducted three times in total to remove the solvent (formamide) in reswollen gel. With the solvent removal, the gel volume contracts and simultaneously the gel is dehydrated.

(Operation of the Reaction for Release of C-Terminal Amino Acids)

Next, into the tube containing a gel slice loading thereon a globin peptide chain which has been subjected to modification and protection by acetylation, there is poured 1 ml of a formamide solution containing 1% by volume of heptafluorobutanoic acid (HFBA: C$_3$F$_7$COOH) and 10% by volume of acetic anhydride. The whole tube is sealed and held at 40° C. for 16 hours in a dry atmosphere with stirring.

During this period, the gel in contraction reswells owing to the infiltration of formamide solvent and returns to its original volume. HFBA and acetic anhydride act on the C-terminus of the peptide chain bound on the reswollen gel, at the above temperature, whereby successive release of C-terminal amino acids of peptide chain proceeds. Specifically explaining, there proceed, at the C-terminus of the peptide, keto-enol tautomerism represented by the following general scheme (Ia), which is promoted by HFBA acting as a proton donor:

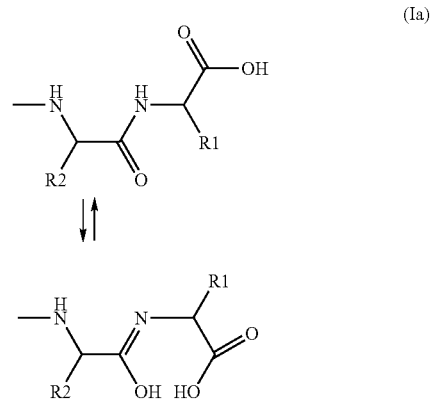

and also acetic anhydride acts on the C-terminal carboxy group; thereby conversion into asymmetric acid anhydride and subsequent formation of cyclic ester proceed, whereby it is converted once into 5-oxazolone ring structure, represented by the following reaction scheme (Ib):

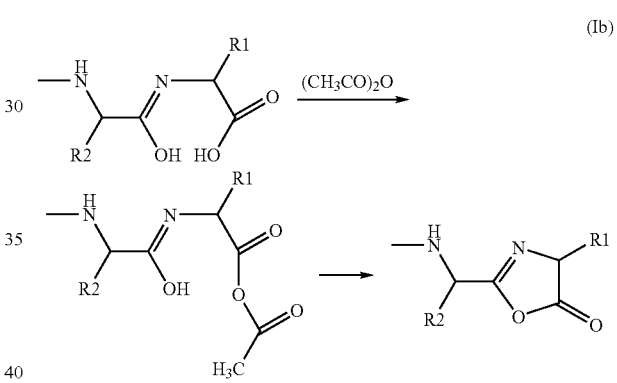

Further, it is presumed that this 5-oxazolone ring undergoes a reaction represented by, for example, the following reaction formula (II'):

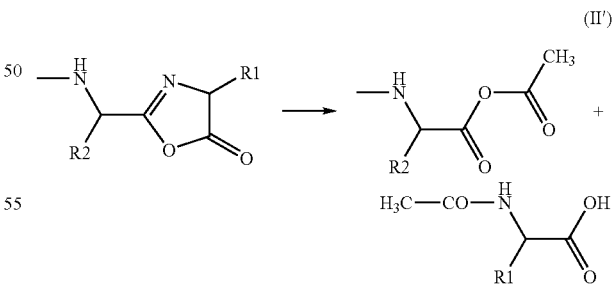

thereby, release of C-terminal amino acids and formation of reaction intermediate for next-stage reaction progress and, in this way, successive release of C-terminal amino acids proceeds.

The successive release of C-terminal amino acids proceeds and, as a result, there remains, in the gel and in a state bound thereon, a mixture of a series of reaction products formed by stepwise release of C-terminal amino acids and an original peptide chain modified and protected by acetylation but yet remaining in 5-oxazolone structure. After the end of said treatment for successive release of C-terminal amino acids, the formamide solution containing unreacted acetic anhydride, HFBA, etc., that remains in the tube is removed; 1 ml of acetonitrile is poured into the tube; stirring is made for 15 minutes. Then, the acetonitrile is discarded; 1 ml of acetonitrile is poured newly; stirring is conducted again for 15 minutes. This extraction of formamide solution in gel by acetonitrile is conducted three times in total to remove the solvent (formamide) in reswollen gel. With the solvent removal, the gel volume contracts and simultaneously the gel is dehydrated.

(Post-Treatment Operation)

Next, into the tube containing a gel slice loading thereon a mixture containing reaction products is poured 1 ml of an aqueous solution containing 10% by volume of DMAE [$(CH_3)_2N-CH_2CH_2OH$]. The whole tube is sealed and is kept at 60° C. for 1 hour with stirring. In this case, the dehydrated gel reswells quickly owing to the infiltration of solvent (water) and returns to its original volume. Water molecules act, in the co-presence of the nitrogen-containing, basic organic compound and at the above temperature, on the peptide chain and reaction products bound on the reswollen gel, whereby hydration proceeds.

As, in the above mixture, the C-termini of reaction products of peptide are in a mixture state including those staying in the 5-oxazolone structure, or being advanced even to an asymmetric acid anhydride therefrom, other than those being converted into carboxy group, the post-treatment is a treatment mainly aiming to convert them into a state where all the C-termini of the peptides have turned carboxy groups by applying treatment for hydrolysis to them. Further, since the nitrogen-containing basic organic compound functions as a basic catalyst, there occur, on the peptide chain modified and protected by acetyl group, hydrolysis and deprotection of the O-acetylation of the hydroxy groups present in the serine residue [—NH—CH($CH_2OH$)—CO—] and the threonine residue [—NH—CH(CH($CH_3$)OH)—CO—], as well as partial hydrolysis of the O-acetylation of the phenolic hydroxy group of tyrosine residue [—NH—CH($CH_2$—$C_6H_4$—OH)—CO—]. However, since the basicity of the organic base used is not high, deprotection of N-acetylation does not proceed and, after the post-treatment, there remain, at a very high selectivity, only the N-acetylation of N-terminal amino group, the N-acetylation of the ε-position amino group of lysine residue [—NH—CH($CH_2CH_2CH_2CH_2NH_2$)—CO—] and, in some cases, the O-acetylation of the phenolic hydroxy group of tyrosine residue [—NH—CH($CH_2$—$C_6H_4$—OH)—CO—].

After such post-treatment, the aqueous solution remaining in the reactor is removed; 1 ml of acetonitrile is poured into the reactor; stirring is made for 15 minutes. Then, the acetonitrile is discarded; 1 ml of acetonitrile is poured newly; stirring is made again for 15 minutes. This extraction of aqueous solution in gel by acetonitrile is conducted three times in total to dehydrate the reswollen gel. With the dehydration, the gel volume contracts.

(Fragmentization of Peptide by Digestion with Trypsin)

The globin peptide chain of horse myoglobin comprises 153 amino acids and its molecular weight deviates from an appropriate molecular weight range of mass spectrometry. Therefore, peptide fragmentization by digestion with trypsin is conducted.

Specifically explaining, into the reactor containing the dehydrated gel slice after the above post-treatment is added an aqueous solution containing trypsin and, in a state of peptide chain bound on gel carrier, fragmentization of the peptide chain is carried out. The aqueous solution containing trypsin is an ammonium bicarbonate buffer solution (pH 8) containing trypsin at a concentration of 0.067 μg/μl. Digestion with trypsin is achieved by stirring at 37° C. for 4 hours to give rise to an enzymatic reaction. In this case, the dehydrated gel reswells quickly owing to the infiltration of solvent (water) and returns to its original volume. At the above temperature, the trypsin, together with the buffer solution, penetrates into the reswollen gel and acts on the peptide chain and reaction products bound on the gel, whereby trypsin-specific enzymatic cleavage proceeds.

Incidentally, in the peptide chain and reaction products, the N-acetylation of N-terminal amino group and the N-acetylation of the ε-position amino group of lysine residue [—NH—CH($CH_2CH_2CH_2CH_2NH_2$)—CO—] remain as such even after the deprotection in the post-treatment; in the digestion with trypsin, the cutting of the C-terminal side peptide bond of N-acetylated lysine residue does not take place and there takes place only the cutting of the C-terminal side peptide bond of alginine residue. The amino acid sequence possessed by the globin peptide chain of horse myoglobin is already known, and the original peptide chain comprising 153 amino acids, shown in FIG. 4, when subjected to digestion with trypsin, produces fragments each containing a partial amino acid sequence of 1-31 amino acids, a partial amino acid sequence of 32-139 amino acids and a partial amino acid sequence of 140-153 amino acids. Therefore, a series of reaction products produced by the successive release of C-terminal amino acids, together with a C-terminal fragment containing the partial amino acid sequence of 140-153 amino acids, give a series of mass spectrum peaks reflecting the molecular weight differences corresponding to C-terminal amino acids. Incidentally, in FIG. 4, the lysine residues to be N-acetylated in the pre-treatment operation are shown in a dotted state; and the partial amino acid sequences of 1-31 amino acids and 140-153 amino acids which are to be produced by the digestion with trypsin of C-terminal side peptide bond of each arginine residue are shown in bold type.

After the digestion with trypsin, peptide fragments dissolving in the trypsin solution in the reactor are recovered from the gel. The solution containing a mixture of recovered peptide fragments is subjected to desalting and then lyophilized in vacuum.

(Identification of Reaction Products Processed by Post-Treatment and Peptide Fragmentization by Means of Trypsin Digestion)

The mixture of the reaction products processed by post-treatment and peptide fragmentization by means of trypsin digestion and the C-terminal fragments of globin peptide chain, which are obtained by completion of a series of treatments, is subjected to mass spectrometry to determine the molecular weight of each peptide fragment contained in the mixture.

In this Example, the dried sample of peptide fragment mixture is subjected to mass spectrometry using a mass spectrometer, specifically a MALDI-TOF-MS apparatus to measure the masses of the main ion species peaks reflecting the molecular weights of individual peptide fragments and the relative peak intensities of the main ion species peaks. Incidentally, in the measurement using the MALDI-TOF-MS apparatus, there is conducted a negative mode measurement wherein negatively charged ion species are introduced into a detector.

Figure 2:
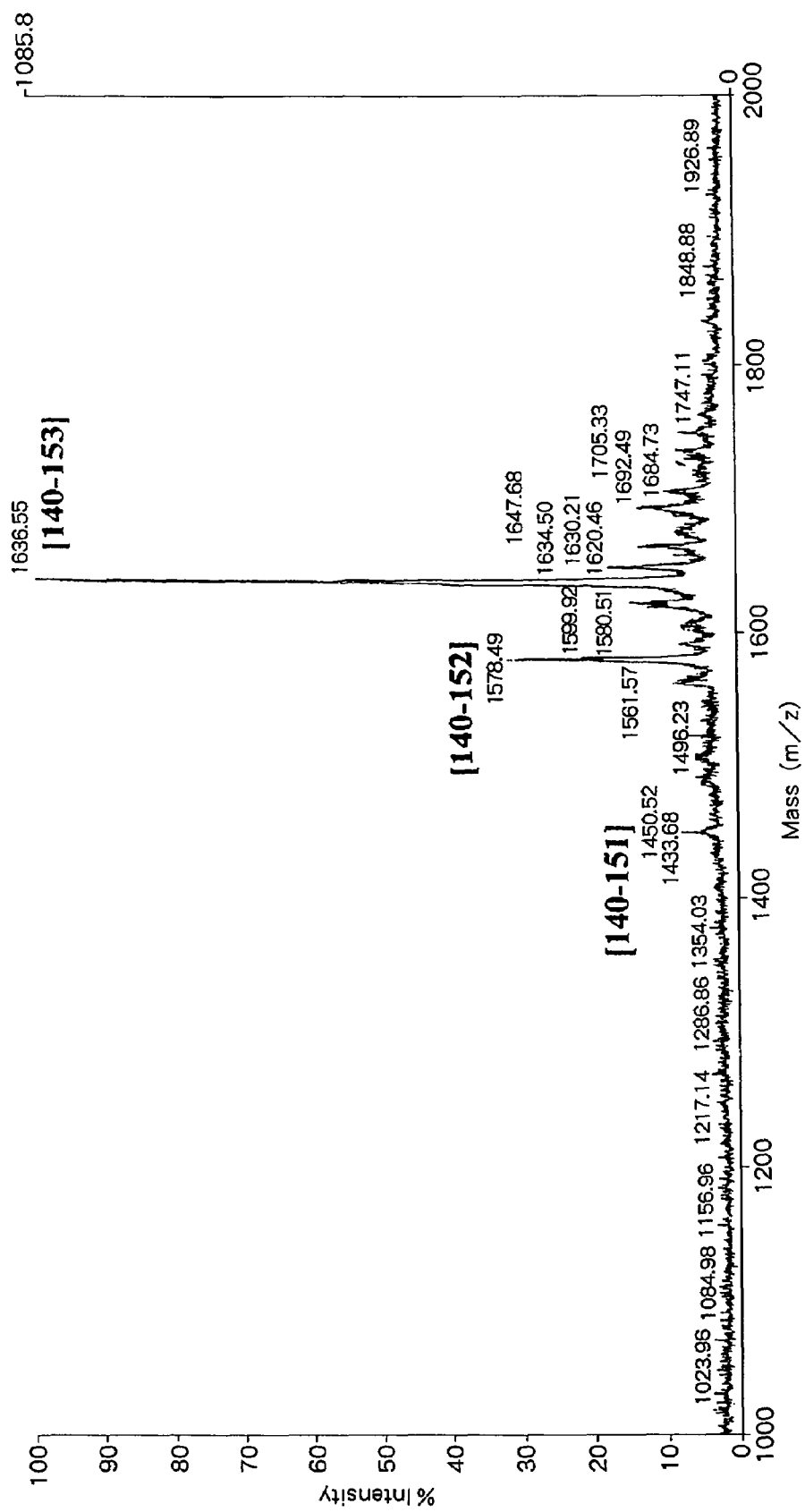
FIG. 2 is a chart showing an example of the mass spectrometry spectrum of a mixture of reaction products that are obtained by successive release of C-terminal amino acids from a globin peptide chain of horse myoglobin by means of the treatment technique for successively releasing the C-terminal amino acids from a peptide according to the present invention.

FIG. 2 shows a mass spectrum obtained for the mixture obtained in the above-mentioned series of treatments of the present Example and containing trypsin-cleaved peptide fragments of the reaction products produced by successive release of C-terminal amino acids. In Table 1 are shown the masses of measured peaks, their differences from the masses of peaks of C-terminal fragments of original globin peptide chain, the amino acids identified therefrom which are removed in individual reaction product fragments, and the structures of individual reaction products.

TABLE 1

| m/Z | Δm | Assignment | Corresponding peptide structure |
|---|---|---|---|
| 1636.55 | — | | NDIAAK(Ac)YK(Ac)ELGFQG |
| 1578.49 | 58.06 | -Gly | NDIAAK(Ac)YK(Ac)ELGFQ |
| 1450.52 | 186.03 | -Gln-Gly | NDIAAK(Ac)YK(Ac)ELGF |

It is confirmed that in the original globin peptide, the partial amino acid sequence of C-terminal fragment consisting of 140-153 amino acids is NDIAAK(Ac)YK(Ac)ELGFQG wherein two lysine residues are N-acetylated at respective side chains and that the series of peaks shown in FIG. 2 correspond to those amino acid sequences formed by successive release of two amino acids: glycine and glutamine from the C-terminus of the above amino acid sequence. That is, it is verified that the to-be-analyzed peptide chain separated as a band on gel slice is truly a globin peptide chain.

Reference Example 1

The method for analysis of the C-terminal amino acid sequence of peptide according to the present invention has the greatest feature in that a to-be-analyzed peptide chain is subjected to a series of reactions in a state separated by gel electrophoresis and bound on the gel carrier used in the electrophoresis. In order to confirm that the analytical accuracy of the present method is essentially equal to a case when a peptide chain itself has been analyzed for C-terminal amino acid sequence, there was conducted, in this Reference Example, C-terminal amino acid sequence analysis for the globin peptide chain of horse myoglobin, in a state that the peptide chain was not bound on a gel carrier.

(Isolation and Preparation of Dried Peptide Powder Sample)

First, there is prepared, using a commercially available horse myoglobin standard sample, a peptide solution containing only the globin peptide chain portion of the standard sample at a concentration of 1.0 μg/μl. The peptide solution is taken into a test tube and lyophilized to prepare a dried peptide powder sample.

(Pre-Treatment Operation)

Then, a vial containing the dried peptide sample is set in a glass-made reactor of air-tight test tube type with fitting stopper, having an evacuation port equipped with a Teflon-made cock valve for sealing. Separately, a given amount of the following liquid reagent is placed in the glass-made reactor. As the reagent for pretreatment, there is used 300 μl of acetic anhydride added with acetic acid at 5% by volume of. After the vial containing the dried peptide sample is set in the glass-made reactor, the reactor inside is evacuated under cooling condition and then sealed in an air-tight state.

The whole reactor of air-tight state is kept at 50° C. for 2 hours to allow acetic anhydride and acetic acid both of vapor state, supplied from the liquid reagent in the reactor, to act on the dried peptide sample. By allowing acetic anhydride as an acylation reagent in the co-presence of acetic acid to act on the dried peptide sample, selective acetylation of the N-terminal amino group of the peptide proceeds. In addition, there take place N-acetylation of the ε-position amino group of the lysine residue [—NH—CH(CH$_2$CH$_2$CH$_2$CH$_2$NH$_2$)—CO—] contained in the peptide chain; O-acetylation of the hydroxy groups present in the serine residue [—NH—CH(CH$_2$OH)—CO—] and the threonine reside [—NH—CH(CH$_3$)OH)—CO—]; and O-acetylation of the phenolic hydroxy group of the tyrosine residue [—NH—CH(CH$_2$—C$_6$H$_4$—OH)—CO—].

After this pre-treatment, the unreacted acetic anhydride, acetic acid, etc. remaining in the reactor are distilled off under reduced pressure, and the resulting protected and modified globin peptide chain is dried.

(Operation of the Reaction for Release of C-Terminal Amino Acids)

Next, in a state that the vial holding the globin peptide chain modified and protected with acetyl group is set in a glass-made reactor of air-tight test tube type with fitting stopper, a given amount of the following liquid reagent is placed anew in the glass-made reactor.

As the liquid reagent for the reaction of successive release of C-terminal amino acids, 300 μl of acetic anhydride containing 1% by volume of heptafluorobutanoic acid (HFBA: C$_3$F$_7$COOH) is used. After the vial containing the dried peptide sample is set in the glass-made reactor, the reactor inside is evacuated under cooling condition and then sealed in an air-tight state.

The whole reactor of air-tight state is kept at 40° C. for 3 hours to allow acetic anhydride and HFBA both of vapor phase, supplied from the liquid reagent in the reactor, to act on the dried peptide sample. Since the HFBA and acetic anhydride are allowed to act on the C-terminus of peptide chain at the above-mentioned temperature, the successive release of the C-terminal amino acids of peptide chain proceeds via the reaction path of the above-mentioned reaction formulas (Ia) to (II') shown in Example 1.

After the completion of the treatment for successive release of C-terminal amino acids, the unreacted acetic anhydride, HFBA, etc. remaining in the reactor are distilled off under reduced pressure and a mixture of the remaining globin peptide chain after protection and modification by acetylation and the reaction products obtained is dried.

(Post-Treatment Operation)

Next, in a state that the vial holding the dried sample of a mixture containing the reaction products is set in a glass-made reactor of air-tight test tube type with fitting stopper, a given amount of the following liquid reagent is placed anew in the glass-made reactor.

As, in the above mixture, the C-termini of reaction products of peptide are in a mixture state including those staying in the 5-oxazolone structure, or being advanced even to an asymmetric acid anhydride therefrom, other than those being converted into carboxy group, the post-treatment is a treatment mainly aiming to convert them into a state where all the C-termini of the peptides have turned carboxy groups by applying treatment for hydrolysis to them. That is, an aqueous solution (300 μl) containing 10% by volume of DMAE is used as a liquid reagent for post-treatment; and after the vial containing the dried peptide sample is set in the glass-made reactor, the reactor inside is evacuated under cooling condition and then sealed in an air-tight state.

The whole reactor of air-tight sealed state is heated at 60° C. for 1 hour to allow the vapor-phase DMAE and water molecules, supplied from the liquid reagent in the reactor, to act on the dried sample. The asymmetric acid anhydride and the 5-oxazolone structure undergo hydrolysis by the action of water molecules in the presence of DMAE as an organic base, whereby they are converted into a form having a carboxy group at the C-terminus. Further, on the peptide chain modified and protected by acetyl group, the O-acetylation of the hydroxy groups present in the serine residue [—NH—CH(CH$_2$OH)—CO—] and the threonine residue [—NH—CH(CH(CH$_3$)OH)—CO—] is hydrolyzed and deprotected, and the O-acetylation of the phenolic hydroxy group of tyrosine residue [—NH—CH(CH$_2$—C$_6$H$_4$—OH)—CO—] is hydrolyzed partially. However, since the basicity of the organic base used is not high, deprotection of N-acetylation does not proceed and, after the post-treatment, there remain, at a very high selectivity, only the N-acetylation of N-terminal amino group, the N-acetylation of the ε-position amino group of lysine residue [—NH—CH(CH$_2$CH$_2$CH$_2$CH$_2$NH$_2$)—CO—] and, in some cases, the O-acetylation of the phenolic hydroxy group of tyrosine residue [—NH—CH(CH$_2$—C$_6$H$_4$—OH)—CO—].

After such post-treatment, the water molecules, DMAE, etc. remaining in the reactor are distilled off under reduced pressure and the mixture of the reaction products after post-treatment is dried.

(Fragmentization of Peptide by Digestion with Trypsin)

The globin peptide chain of horse myoglobin comprises 153 amino acids and its molecular weight deviates from a molecular weight range appropriate for mass spectrometry; therefore, the globin peptide chain is subjected to peptide fragmentization by digestion with trypsin.

Specifically explaining, the dried sample of a mixture containing reaction products after post-treatment is placed in a reactor, and an aqueous solution containing trypsin is added to conduct fragmentization of peptide chain. The aqueous solution containing trypsin is a 3-pyridine acetate buffer solution (pH: 7) containing 0.1 μg/μl of trypsin. The mixture is stirred at 37° C. for 8 hours to conduct an enzymatic reaction, whereby digestion with trypsin takes place.

Incidentally, in the original peptide chain and reaction products, the N-acetylation of N-terminal amino group and the N-acetylation of the ε-position amino group of lysine residue [—NH—CH(CH$_2$CH$_2$CH$_2$CH$_2$NH$_2$)—CO—] remain as such even after the deprotection in the post-treatment; in the digestion with trypsin, the cutting of the C-terminal side peptide bond of N-acetylated lysine residue does not take place and there takes place only the cutting of the C-terminal side peptide bond of arginine residue. The amino acid sequence possessed by the globin peptide of horse myoglobin is already known, and the original peptide chain comprising 153 amino acids, when subjected to digestion with trypsin at the arginine residues, produces fragments each containing a partial amino acid sequence of 1-31 amino acids, a partial amino acid sequence of 32-139 amino acids, or a partial amino acid sequence of 140-153 amino acids. Therefore, a series of reaction products produced by the above-mentioned successive release of C-terminal amino acids, together with a C-terminal fragment containing a partial amino acid sequence of 140-153 amino acids, give a series of mass spectrum peaks reflecting the molecular weight differences corresponding to C-terminal amino acids.

After the digestion with trypsin, the reaction mixture is subjected to desalting using ZipTip and then to separation and recovery of peptide fragments. These peptide fragments are subjected to lyophilization.

(Identification of Reaction Products Processed by Post-Treatment and Peptide Fragmentization by Means of Trypsin Digestion)

The mixture of the reaction products processed by post-treatment and peptide fragmentization by means of trypsin digestion and the C-terminal fragments of globin peptide chain, which are obtained by completion of a series of treatments, is subjected to mass spectrometry to determine the molecular weight of each peptide fragment contained in the mixture.

In this Reference Example, the dried sample of peptide fragment mixture is subjected to mass spectrometry using a mass spectrometry apparatus, i.e. a MALDI-TOF-MS apparatus to measure the masses of the main ion species peaks reflecting the molecular weights of individual peptide fragments and the relative peak intensities of the main ion species peaks. Incidentally, in the measurement by the MALDI-TOF-MS apparatus, there is conducted a negative mode measurement wherein negatively charged ion species are introduced into a detector.

FIG. 3 shows a mass spectrum obtained for the mixture obtained in the above-mentioned series of treatments of the present Reference Example and containing trypsin-cleaved peptide fragments of the reaction products produced by successive release of C-terminal amino acids. In Table 2 are shown the masses of measured peaks, their differences from the masses of peaks of C-terminal fragments of original globin peptide chain, the amino acids identified therefrom which are removed in individual reaction product fragments, and the structures of individual reaction products.

TABLE 2

| m/Z | Δm | Assignment | Corresponding peptide structure |
|---|---|---|---|
| 1636.58 | — | | NDIAAK(Ac)YK(Ac)ELGFQG |
| 1578.55 | 58.03 | -Gly | NDIAAK(Ac)YK(Ac)ELGFQ |
| 1449.58 | 187.00 | -Gln-Gly | NDIAAK(Ac)YK(Ac)ELGF |
| 1302.58 | 334.00 | -Phe-Gln-Gly | NDIAAK(Ac)YK(Ac)ELG |
| 1245.74 | 390.84 | -Gly-Phe-Gln-Gly | NDIAAK(Ac)YK(Ac)EL |

In the treatment of the present Reference Example using a vapor-phase reagent, the successive release of C-terminal amino acids gives a series of reaction products formed by elimination of four amino acids, i.e. glycine, glutamine, phenylalanine and glycine. Besides the peaks of the C-terminal peptide fragment containing the partial amino acid sequence of 140-153 amino acids, etc., there are observed two peaks (m.w.: 2996.18, 3485.48) of peptide fragments of 1-31 amino acid portion and 78-102 amino acid portion, produced by digestion with trypsin. Incidentally, the fragment of 78-102 amino acid portion is a fragment formed by deprotection of part of N-acetylated amino groups in hydrolysis and subsequent digestion with trypsin at the deprotected site.

Incidentally, a series of peaks shown in Table 1 and Table 2, obtained after the successive release of C-terminal amino acids show good correspondence to each other, and it is confirmed that substantially the same analytical accuracy is obtained even when the successive release of C-terminal amino acids is conducted in a state that a to-be-analyzed peptide chain has been bound on a gel, according to the method of the present invention for analysis of the C-terminal amino acid sequence of peptide.

INDUSTRIAL APPLICABILITY

In the method for analysis of the C-terminal amino acid sequence of peptide according to the present invention, there is used, as the technique for successively releasing the C-terminal amino acids of peptide, a process which comprises steps of subjecting a target peptide beforehand to gel electrophoresis for separation; dehydrating the gel carrier used in the gel electrophoresis; in a state that the peptide has been bound thereon, by using a polar aprotic solvent, immersing the gel carrier which has shrunk owing to the dehydration, in a mixed solution of an alkanoic acid anhydride with a small amount of a perfluoroalkanoic acid in relative ratio thereto dissolved in a dipolar aprotic solvent that is infiltratable into the gel substance and capable of keeping the gel substance in a swollen state, to reswell the gel carrier at a temperature selected in a range of 30° C. to 80° C. and moreover allow the alkanoic acid anhydride and the perfluoroalkanoic acid to act on the target peptide sample bound on the gel carrier, thereby C-terminal amino acid is released in association with cleavage of the 5-oxazolone ring, through the formation of 5-oxazolone ring structure, to produce a series of reaction products. In this technique, since the reactivity of the alkanoic acid anhydride per se used therein is low, there occurs no undesired side reactions such as cutting of peptide bond in the middle of peptide chain, and successive release of the C-terminal amino acids of peptide is possible. Further, by conducting the reaction under such mild conditions, the process provides the more superior adjustment and controllability of the maximum amino acid length of C-terminal amino acid sequence that is truncated, which is attained in the series of reaction products obtained thereby. Thus, the present method has advantages of excellent controllability in the successive release of C-terminal amino acids of peptide and mild reaction conditions, for instance, broad width of acceptable variation for the reaction temperature. In addition, The present method has further advantages in practical application; that is, since the target peptide is beforehand isolated by gel electrophoresis, and then it is analyzed in a state bound on the gel carrier, complicated operations for separation and recovery of peptide from gel carrier can be omitted and, moreover, sample loss caused by low yield ratio in the separation and recovery can be avoided. Therefore, the method for analysis of the C-terminal amino acid sequence of peptide according to the present invention can be used as analyzing procedure with wider applicability.

The invention claimed is:

1. A method for analyzing the C-terminal amino acid sequence of a peptide being maintained in a state that it is bound on a gel carrier, which method comprises steps of:
    releasing the C-terminal amino acids successively from the peptide being bound on the gel carrier by chemical procedure to prepare a mixture containing said original peptide and a series of peptidyl reaction products produced therefrom,
    analyzing the original peptide and said series of the peptidyl reaction products produced at the releasing step by means of mass spectrometry to measure the decreases in molecular weight associated with the successive release of the C-terminal amino acid, and
    identifying a series of the C-terminal amino acids removed successively, based on a series of the measured decreases in molecular weight,
    wherein the gel carrier is a polyacrylamide gel, and
    the releasing step comprises:
    a sub-step (1) of conducting dehydration treatment for removing out the water solvent impregnated into the gel carrier,
    a sub-step (2) of immersing the gel carrier, on which the peptide is still bound after said step of dehydration treatment, in a mixed solution of an alkanoic acid anhydride and a perfluoroalkanoic acid dissolved in a dipolar aprotic solvent to allow the alkanoic acid anhydride and the perfluoroalkanoic acid to act on the peptide being kept in the bound state; and
    a sub-step (3) of removing the mixed solution from the gel carrier by dilution with use of a polar aprotic solvent;
    wherein in the sub-step (2),
    the successive release of the C-terminal amino acids results from the reaction process with use of the mixed solution in which formed is a 5-oxazolone-ring structure represented by the following general formula (111):

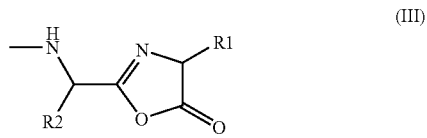

where R1 is a side chain of the C-terminal amino acid of the peptide and R2 is a side chain of the amino acid residue positioned just before the C-terminal amino acid, followed by the cleavage of the 5-oxazolone-ring.

2. A method claimed in claim 1, wherein a concentration of the alkanoic acid anhydride contained in the mixed solution is selected in a range of 10 to 30% by volume.

3. A method claimed in claim 1, wherein the sub-step (2) is carried out at a temperature selected in a range of 30° C. to 80° C.

4. A method claimed in claim 1, wherein a symmetric anhydride of an alkanoic acid having 2 to 4 carbon atoms is used as the alkanoic acid anhydride contained in said mixed solution.

5. A method claimed in claim 1, wherein acetic anhydride is used as the alkanoic acid anhydride contained in the mixed solution.

6. A method claimed in claim 1, wherein a perfluoroalkanoic acid of which a pKa is in the range of 0.3 to 2.5 is used as the perfluoroalkanoic acid contained in the mixed solution.

7. A method claimed in claim 1, wherein a perfluoroalkanoic acid having 2 to 4 carbon atoms is used as the perfluoroalkanoic acid contained in the mixed solution.

8. A method claimed in claim 1, wherein in the mixed solution, the content ratio of the alkanoic acid anhydride and the perfluoroalkanoic acid is selected in the range of 1 to 20 volumes of the perfluoroalkanoic acid per 100 volumes of the alkanoic acid anhydride.

9. A method claimed in claim 1, wherein, in the sub-step (2), the reaction system in which the alkanoic acid anhydride and the perfluoroalkanoic acid act on the peptide is kept in a dry atmosphere wherein not only water but also oxygen have been eliminated.

10. A method claimed in claim 1, wherein the releasing step further comprises the following two substeps after the sub-step (3):
    a sub-step (4) of hydrolysis treatment, in which the hydrolysis treatment for said mixture comprising the original peptide and the series of peptidyl reaction products is conducted by immersing the gel carrier in an aqueous solution dissolving a basic nitrogen-containing aromatic compound or a tertiary amine compound therein to allow a water molecule to act, in the presence of said basic nitrogen-containing organic compound, on the original peptide and the series of peptidyl reaction products being still bound on the gel carrier; and
    a sub-step (5) of redehydration treatment, in which the redehydration treatment for the gel carrier is performed by removing said aqueous solution infiltrated into the gel carrier by dilution with use of a polar aprotic solvent.

11. A method claimed in claim 1, wherein the releasing step further comprises the following two sub-steps for pretreatment before the sub-step (2):
- a sub-step (6) of N-acylation protection, in which applying N-acylation protection to the N-terminal amino group of the peptide is conducted by immersing the gel carrier in a solution of an alkanoic acid anhydride dissolved in a dipolar aprotic solvent to allow the alkanoic acid anhydride to act on the peptide that is kept in the bound state; and
- a sub-step (7) of termination of the N-acylation reaction, in which removal of said solution of the alkanoic acid anhydride is carried out by dilution with use of a polar aprotic solvent to conduct the termination of the N-acylation reaction.

12. A method claimed in claim 1, wherein the peptide being maintained in a state that it is bound on the gel carrier has been in advance subjected to separation by gel electrophoresis.

13. A method claimed in claim 4, wherein a symmetric anhydride of a linear-chain alkanoic acid having 2 to 4 carbon atoms is used as said symmetric anhydride of an alkanoic acid having 2 to 4 carbon atoms.

14. A method claimed in claim 6, wherein a linear-chain perfluoroalkanoic acid having 2 to 4 carbon atoms is used as the perfluoroalkanoic acid having 2 to 4 carbon atoms.

15. A method claimed in claim 11, wherein the same alkanoic acid anhydride is employed for the alkanoic acid anhydride used in the sub-step (6) of N-acylation protection as well as for the alkanoic acid anhydride used in the sub-step (2).

16. A method claimed in claim 1, wherein a MALDI-TOF type mass spectrometry is selected as the mass spectrometry.

* * * * *